US011446270B2

(12) United States Patent
Zhu et al.

(10) Patent No.: US 11,446,270 B2
(45) Date of Patent: Sep. 20, 2022

(54) LEONURINE CRYSTAL AND USE THEREOF IN PREPARATION OF INSULIN SENSITIZER, HYPOGLYCEMIC DRUG AND LIPID-LOWERING DRUG

(71) Applicant: ZHUHAI HENGQIN NEW DISTRICT ZHONGZHU ZHENGTAI MEDICAL MANAGEMENT CO. LTD., Zhuhai (CN)

(72) Inventors: Yichun Zhu, Shanghai (CN); Yizhun Zhu, Shanghai (CN); Xinhua Liu, Shanghai (CN); Ying Chen, Shanghai (CN); Rinkiko Suguro, Shanghai (CN); Yanfei Zhang, Shanghai (CN)

(73) Assignee: ZHUHAI HENGQIN NEW DISTRICT ZHONGZHU ZHENGTAI MEDICAL MANAGEMENT CO., LTD., Zhuhai (CN)

( * ) Notice: Subject to any disclaimer, the term of this patent is extended or adjusted under 35 U.S.C. 154(b) by 0 days.

(21) Appl. No.: 16/491,105

(22) PCT Filed: Sep. 18, 2018

(86) PCT No.: PCT/CN2018/106207
§ 371 (c)(1),
(2) Date: Oct. 22, 2019

(87) PCT Pub. No.: WO2019/080671
PCT Pub. Date: May 2, 2019

(65) Prior Publication Data
US 2020/0069633 A1 Mar. 5, 2020

(30) Foreign Application Priority Data
Oct. 23, 2017 (CN) .......................... 201710995455.5

(51) Int. Cl.
*A61K 31/24* (2006.01)
*A61P 9/10* (2006.01)
*A61P 3/06* (2006.01)
*A61P 3/10* (2006.01)

(52) U.S. Cl.
CPC ................ *A61K 31/24* (2013.01); *A61P 3/06* (2018.01); *A61P 3/10* (2018.01); *A61P 9/10* (2018.01); *C07B 2200/13* (2013.01)

(58) Field of Classification Search
CPC ......... A61K 31/235; A61K 31/24; A61P 3/00; A61P 3/04; A61P 3/06; A61P 3/10; A61P 3/20
USPC ....................................................... 514/534
See application file for complete search history.

(56) References Cited

FOREIGN PATENT DOCUMENTS

| CN | 1415603 A | 5/2003 |
|---|---|---|
| CN | 101732303 A | 6/2010 |
| CN | 102260198 | * 11/2011 |
| CN | 102579420 A | 7/2012 |
| CN | 103565786 A | 2/2014 |
| CN | 108129355 A | 6/2018 |
| CN | 108261412 A | 7/2018 |
| CN | 108276308 A | 7/2018 |

OTHER PUBLICATIONS

Machine translation CN 1415603, 2003.*
Huang, Hui, "Preliminary Study on the Therapeutic Effect of Leonurine (SCM-198) on Type 2 Diabetes Mellitus and Its Possiblle Mechanism," Medicine & Public Health, No. 08, Aug. 15, 2012, pp. 1674-0246.
International Search Report dated Dec. 25, 2018 in PCT/CN2018/106207.
Written Opinion dated Dec. 25, 2018 in PCT/CN2018/106207.
First Office Action of CN201710995455.5 dated Dec. 11, 2020.
Second Office Action of CN201710995455.5 dated Jun. 10, 2021.
Extended European Search Report of EP18870310.2 dated Nov. 10, 2020.
Replaced European Search Report of EP18870310.2 dated May 18, 2021.
Kim Jangseon et al: "Inhibitory effects of Leonurus Sibiricuson weight gain after menopause in ovariectomized and high-fat diet-fed mice", Journal of Natural Medicines, Japanese Society of Pharmacognosy, vol. 70, No. 3, pp. 522-530 Feb. 22, 2016.
Liu Yanzhuo et al: "Inhibition of COX-2/mPGES-1 and 5-LOX in macrophages by leonurine ameliorates monosodium urate crystal-induced inflammation", Toxicology and Applied Pharmacology, vol. 351, pp. 1-11 Jul. 1, 2018.
Decision of Refusal of CN201710995455.5 Mar. 9, 2022.

* cited by examiner

*Primary Examiner* — Ana Z Muresan
(74) *Attorney, Agent, or Firm* — Muncy, Geissler, Olds & Lowe, P.C.

(57) ABSTRACT

This invention belongs to the modern pharmaceutical field of Traditional Chinese Medicine, and relates to an herbal extract of Chinese Motherwort and its application in pharmacy, which specifically relates to the crystal structure of a Chinese Motherwort extract: Leonurine, and its application in the preparation of medicine. The chemical name of the above-mentioned Leonurine is 4-guanidino-1-)butyl 4-hydroxy-3,5-dimethoxybenzoate. The invention by specific methods prepares leonurine as 6 kinds of crystals with different crystal forms. Specifically, there are six different structures of leonurine sulfate crystals, two of them are hydrate, two are anhydrous crystal form, one is methanol solvate, one is ethanol solvate. The leonurine crystal forms of this invention can applicate in preparing medicine such as insulin sensitizer, hypoglycemic and lipid-lowering drugs. The above mentioned insulin sensitizers are particularly useful in treating insulin resistance syndrome, and the above mentioned lipid-lowering drugs are useful in the treatment of disorders of lipid metabolism, hyperlipidemia and their complications.

5 Claims, 15 Drawing Sheets

LEONURINE CRYSTAL AND USE THEREOF IN PREPARATION OF INSULIN SENSITIZER, HYPOGLYCEMIC DRUG AND LIPID-LOWERING DRUG

BACKGROUND OF THE INVENTION

(1) Field of the Invention

This invention belongs to the field of modern pharmacy of Traditional Chinese Medicine, and relates to an herbal extract of Chinese Motherwort and its application in pharmacy, which specifically relates to the crystal structure of an herbal extract, leonurine, of a Chinese Motherwort extract, and its application in the preparation of medicine, especially the use in the preparation of insulin sensitizer, hypoglycemic and lipid-lowering drug. The above mentioned insulin sensitizers are particularly useful in treating insulin resistance syndrome, and the above mentioned lipid-lowering drugs are particularly useful in the treatment of disorders of lipid metabolism, hyperlipidemia and their complications.

(2) Description of Related Art

The existing technology discloses that substances of atoms, molecules, or ions arranged regularly and periodically of constituent substances are called crystals; the above mentioned crystal is mostly solid except for liquid crystal. The main technique for identifying the structure of crystals at present is X-ray diffraction. Related studies can use the scattering effect of electrons on X-rays to obtain the distribution of electron density in the crystal, and then obtain the position information of the atom by crystallographic analysis, that position information is the crystal structure. Generally, the particles (atoms, ions, molecules, and atomic groups) in the internal structure of the crystal are arranged regularly and periodically in a three-dimensional space to form a lattice of a specific morphology. In view of the regularity and repeatability of the arrangement of atoms inside crystal, a minimum unit that can fully express the lattice structure and can be taken from the crystal lattice, is called a unit cell. If the particles (atoms, ions, molecules, and atomic groups) of certain substance do not have the above mentioned regular arrangement, but is arranged in a disorderly form, it is called amorphous.

Studies have confirmed that crystals of a substance can provide it with unique physical and chemical characteristics, such as graphite and diamond are different crystals of the elemental carbon. Due to the different crystal form, the physical and chemical characteristics of the two are greatly different. Several monomeric chemical drugs can also form one or more crystal structures, and the formation of drug crystals has a significant impact on their physical, chemical, and biological properties. Studies have reported that the drug crystal form has a significant effect on the chemical stability, pharmacokinetics, and even pharmacological and toxicological effect of the drug. The industry believes that different crystal forms of the same chemical can have different physical and chemical characteristics and can also produce different pharmacological effects. Therefore, the preparation of drug crystal forms is of great value for the creation of new drugs with controllable quality.

Studies have reported that insulin resistance syndrome is because of the reactivity and sensitivity of the body to the physiological effects of insulin are reduced, and thus a series of functional, structural disorders and pathological diseases of the body is caused. The industry believes that the syndrome is actually a decrease in the signal transduction function of the insulin receptor and its downstream signaling pathways, resulting in insulin not effectively activating insulin receptors in its target organs such as liver, skeletal muscle and fat; thereby insulin loses or reduces its physiological effects, causing metabolic disorders and excessive insulin levels in the body. Therefore, a special phenomenon has been formed that the insulin level in the body is higher than the normal value but the physiological effect caused by insulin is decreased. Clinical practices show that if the disease is not treated in time, the body will have glucose metabolism disorders due to insulin receptor dysfunction, and subsequently, lipid metabolism disorder, hypertension, hyperviscosaemia, obesity and other secondary diseases will be occured. These secondary diseases will further cause endothelial dysfunction, vascular injury, atherosclerosis, and damage to important organs such as heart, brain and kidney. On the other hand, due to the decreased sensitivity of the body to insulin, the synthesis and secretory compensatory of insulin in the body are increased, thereby resulting in hyperinsulinemia, and the excessive insulin in the body for a long time will lead to the reconstruction and damage of important organs and blood vessels. Therefore, insulin resistance syndrome is a serious basic disease, which is also a considerable part of diabetes, hyperlipidemia, hyperviscosaemia, obesity and hypertension (including secondary blood vessels and important organ damage). The basis and reason. In other words, the clinical manifestations of hyperglycemia, hyperlipidemia, obesity, and hypertension in several patients are the appearance, and the real cause is insulin resistance. If a therapy targets these results including yperglycemia, hyperlipidemia, obesity, and hypertension, rather than insulin resistance, the underlying cause, even though laboratory findings such as blood sugar, blood lipid, blood viscosity and blood pressure can improve temporarily, however, if the insulin resistance as the underlying primary disease has not been alleviated, the long-term effects of the above symptomatic treatment are poor, especially, the most important organ damage is difficult to be improved. The industry believes that only by solving the problem of insulin resistance fundamentally is the treatment to this major and popular major diseases. In fact, the concept of precise medicine raised in recent years pointed out that carring on individualized etiological treatment, according to the different pathogenesis of different individuals and no longer limited to the previous symptomatic treatment holds the same view of Traditional Chinese Medicine. This concept can be traced back to the idea of "treatment based on syndrome differentiation", "the same disease with different treatments" and "the different diseases with same treatment" posed by Traditional Chinese Medicine more than one thousand years ago. For example, insulin resistance can lead to diabetes, and can further lead to other diseases such as hyperlipidemia, obesity, high blood pressure, etc. as well, by "the different diseases with same treatment", to treat their common primary disease (insulin resistance syndrome) of said ostensibly different diseases with insulin sensitization therapy for relieving insulin resistance to said common primary underlying disease, then hyperglycemia, hyperlipidemia, obesity, hyper viscosity, hypertension and other secondary diseases can be solved. On the other hand, clinical studies have shown that diabetic patients are not all caused by insulin resistance, through a series of tests different subgroups with or without insulin resistance for different treatments ("treatment based on syndrome differentiation") are able to be distinguished. Subgroup caused by insulin resistance is suitable for insulin sensitization therapy, which is called "the different diseases with same treatment". From the modern precise medicine point of view, the diseases of high blood sugar, hyperlipidemia, obesity, hypertension, etc., which are concerned in the present invention, need to be tested first, and those caused by insulin resistance should be treated accordingly by the etiological treatment of improving the insulin resistance.

Clinical practice shows that the above problems have indeed received much attention in the past years, and insulin sensitizer is presented, which was specifically used to treat insulin resistance syndrome. This provide a powerful technical means for the implementation of etiological treatment of precision medicine. The above mentioned insulin sensitizer is a thiazolidinedione derivative, and the first drug is Troglitazone (trade name Rezulin), which was once highly hoped by the medical community and believed to be effective drug for etiological treatment for insulin resistance syndrome, but the hepatotoxicity and cardiovascular events including heart failure and severe edema caused by it have led to a global withdraw since 2000. No high-efficiency and low-toxic alternative drugs are available after that.

The Chinese herbal medicine Motherwort (Origanum, Herba Leonuri, Chinese Motherwort) was first included in the ancient books such as "Shen Nong's Herbal Classic" and "Compendium of Materia Medica". It has the effects of promoting blood circulation, detumescence and diuresis, regulating menstruation. According to The Pharmacopoeia of the People's Republic of China (2000 edition), the Chinese Motherwort can be used for the treatment of irregular menstruation, dysmenorrhea, amenorrhea, incomplete lochia, edema, oliguria and acute nephritis edema, etc. There is no report about the application of leonurine crystals as insulin sensitizers. Previous studies of this application have found that the Chinese Motherwort has a series of new uses in addition to the above-mentioned known functions, including cardiovascular protection, etc., and have further separated and synthesized the monomeric active ingredient of leonurine, which determined it as drug candidate and some other new uses. However, the crystal structure of the leonurine have not been resolved, based on this, the inventors of this application intend to provide the crystal structure of the leonurine and provide a new use of the dominant pharmaceutical crystal form in the preparation of the drug. The uses of leonurine crystals involved are specifically insulin sensitizer and regulator of lipid metabolism disorder. The above mentioned insulin sensitizer is especially useful for treating various diseases caused by decrease in insulin sensitivity of the body, including diabetes and insulin resistance syndrome.

On the other hand, atherosclerosis is an important underlying disease leading to myocardial ischemia and myocardial infarction. If it can be prevented effectively, it will greatly reduce the morbidity and mortality of cardiovascular diseases.

At present, atherosclerosis is mainly prevented by clinical application of lipid-lowering drugs. The existing clinical lipid-lowering drugs are mainly statins, including simvastatin and atorvastatin, etc. The drawback of these drugs is that the side effects caused by long-term medication are very serious. Therefore, it has important clinical application value to find safe, effective and low-toxic anti-atherosclerotic drugs.

Leonurine, the monomer active ingredient of the Chinese Motherwort described in this invention, has the characteristics of low toxicity and high safety. The leonurine crystals described in this invention were not reported previously. In particular, the dominant crystal form of them is not only structurally stable, but also has the characteristics of superior medical crystal form, and has good lipid-lowering or anti-atherosclerosis effects. This invention intends to provide lipid-lowering drugs and anti-atherosclerosis drugs prepared by the above mentioned leonurine crystals.

BRIEF SUMMARY OF THE INVENTION

The object of the present invention is to provide a crystal structure of leonurine extracted from the Chinese herbal medicine Chinese Motherwort and its application in preparing medicine based on the current status of the present techniques, especially in preparing insulin sensitizers, hypoglycemic agents and lipid metabolism regulators. The above mentioned insulin sensitizer is especially suitable for treating insulin resistance syndrome, and lipid metabolism regulator is particularly useful for treating lipid metabolic disorders, hyperlipidemia and its complications.

Specifically, the present invention provides an active ingredient of the Chinese herbal medicine Chinese Motherwort, Leonurine and its new pharmaceutical application in preparing insulin sensitizers, hypoglycemic agents, drugs for treating insulin resistance syndrome, lipid-lowering drugs and anti-atherosclerosis drugs.

Another object of this invention is to use the above active ingredient as a raw material for a pharmaceutical preparation.

The further purpose of this invention is to provide the application of the leonurine crystals in the preparation of the treatment of various diseases caused by insulin sensitivity reduction, including the application in pharmaceutical compositions of diabetes, insulin resistance syndrome and hyperlipidemia.

The leonurine crystals mentioned in this invention is an active ingredient of the Chinese Motherwort, and then prepared by mass synthesis. The chemical structural formula is:

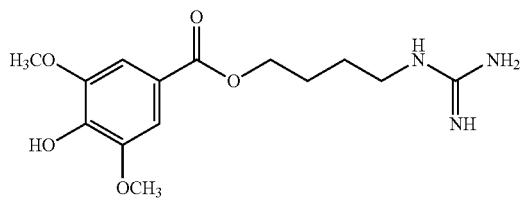 [SMILES: COc1cc(C(=O)OCCCCNC(=N)N)cc(OC)c1O]

The chemical name of the above-mentioned leonurine: 4-guanidino-1-butyl 4-hydroxy-3,5-dimethoxybenzoate.

The invention prepares leonurine as 6 kinds of crystal with different crystal forms by specific methods. Specifically, they are six different structures of leonurine sulfate crystals, two of them are hydrate, two are anhydrous crystal form, one is methanol solvate, and one is ethanol solvate.

In order to make it easy for description and understanding, the 6 kinds of above-mentioned leonurine crystals are named crystal form A, crystal form B, crystal form C, crystal form D, crystal form E and crystal form F respectively.

The above leonurine crystals have the following characteristics:

(1) Crystal Form A:

Monohydrous crystal form (single crystal structure confirmed), square block crystal; no crystal transformation before melting. The crystal form dehydrated and converted to anhydrous crystal form B at 120-150° C., and started to decompose at about 250° C. In a range of 0-95% relative humidity, the crystal form didn't change and the hygroscopicity thereof changed slightly that no or almost no hygroscopicity is shown. Under the condition of, in the 25° C. suspension experiment, in solutions including methanol, ethanol, isopropanol, acetone, acetonitrile, tetrahydrofuran, nitromethane, ethyl acetate, isopropyl acetate, isopentyl alcohol, methyl tert-butyl ether, toluene, methyl isobutyl ketone, n-hexane, n-heptane, ethyl ether, dichloromethane, trichloromethane, petroleum ether, water, etc.; in the 50° C. suspension experiment, in solutions including methanol, ethanol, acetone, methyl ethyl ketone, isopropyl acetate, methyl tert-butyl ether, toluene, n-hexane, n-heptane, ethyl ether, trichloromethane, petroleum ether, water, etc.; or in the 25° C. and 50° C. suspension experiment with volatilization in most of solvent mixtures, the crystal form A can be obtained.

(2) Crystal Form B:

Anhydrous crystal form, the melting point of the crystal form: $T_{onset}$=190.8° C.; the crystal form had no crystal transformation before melting, and started to decompose at about 230° C. In a range of 0~95% relative humidity, the crystal form changed into crystal form A, and the hygroscopicity changed slightly, showing slightly hygroscopicity; in the 50° C. suspension experiment, under the condition of in solutions including isopropyl alcohol, acetonitrile, tetrahydrofuran, nitromethane, ethyl acetate, isopentyl alcohol, methyl isobutyl ketone, dichloromethane, etc.; or under the condition of 120-150° C. heating and dehydration of crystal form A, the crystal form B can be obtained.

(3) Crystal Form C:

Methanol solvate, with crystal transformation before melting. The crystal form converted to anhydrous crystal form B at 120-160° C., and started to decompose at about 235° C.; in a range of 0~95% relative humidity, the crystal form changed into crystal form A. In the 25° C. suspension experiment, under the condition of methanol and n-hexane (V:V=1:1), methanol and n-heptane (V:V=1:1), methanol and methyl tertiary butyl ether (V:V=1:1), methanol and toluene (V:V=1:1), methanol and methyl isobutyl ketone (V:V=1:1), methanol and methyl tertiary butyl ether (V:V=1:2) and methyl alcohol and toluene (V:V=1:2), etc.; and in the 50° C. suspension experiment, under the condition of methanol and methyl tert-butyl ether (V:V=1:2), methanol and toluene (V:V=1:2), methanol and methyl isobutyl ketone (V/V=1/1), etc., the crystal form C can be obtained.

(4) Crystal Form D:

Ethanol solvate, the crystal form dehydrated and converted to anhydrous crystal form B at 120-150° C., and started to decompose at 250° C.; in a range of 0~95% relative humidity, the crystal form changed into crystal form A. In the 50° C. suspension experiment, under the condition of ethanol and toluene (V/V=1/1), ethanol and toluene (V/V=1/2), etc., the crystal form D can be obtained under the above conditions.

(5) Crystal Form E:

Monohydrous crystal form, the crystal form dehydrated and converted to anhydrous crystal form B at 120-150° C., and started to decompose at 250° C. In a range of 0~95% relative humidity, the crystal form didn't change but the hygroscopicity changed, showing a slight hygroscopicity. In the 25° C. suspension experiment, under the condition of isopropanol and water (V/V=2/1), isopropanol and water (V/V=1/1), isoamyl alcohol and water (V/V=1/1), tetrahydrofuran and water (V/V=2/1); in the 50° C. suspension experiment, under the condition of ethanol and water (V/V=2/1), isopropanol and water (V/V=2/1), isoamyl alcohol and water (V/V=2/1), nitromethane and water (V/V=2/1), toluene and water and methanol (V/V/V=2/1/1), methanol and water (V/V=1/1), isopropanol and water (V/V=1/1), etc., the crystal form E can be obtained.

(6) Crystal Form F:

Anhydrous crystal form, the melting point of the crystal form: $T_{onset}$=192.2° C., with crystal transformation before melting. The crystal form dehydrated and converted to anhydrous crystal form B at 120-150° C., and started to decompose at 250° C. In a range of 0~95% relative humidity, the crystal form changes into crystal form A, and the hygroscopicity changed, showing slightly hygroscopicity. The 60° C. methanol saturated solution could be crystallized by cooling at 4° C. to obtain crystal form F.

In the present invention, according to the relationship between the above performance and druggability, it is recommended that the most stable crystal form A for accelerating experiments(40° C./75% RH) is the medicinal crystal form of leonurine sulfate.

In order to further identify the characteristics of the above 6 kinds of leonurine crystal form, the invention conducts X-ray powder diffraction (XRPD) analysis and obtains the XRPD data as described in the following table 1:

TABLE 1

XRPD data of six kinds of leonurine crystals:

| Crystal form A | | Crystal form B | | Crystal form C | | Crystal form D | | Crystal form E | | Crystal form F | |
| --- | --- | --- | --- | --- | --- | --- | --- | --- | --- | --- | --- |
| 2-Theta | Relative intensity (%) | 2-Theta | Relative intensity (%) | 2-Theta | Relative intensity (%) | 2-Theta | Relative intensity (%) | 2-Theta | Relative intensity (%) | 2-Theta | Relative intensity (%) |
| 5.26 | 18.6 | 5.73 | 9.3 | 7.55 | 14.3 | 6.57 | 16.4 | 5.46 | 17.7 | 5.44 | 53.0 |
| 7.24 | 13.6 | 8.79 | 9.3 | 11.88 | 100.0 | 10.45 | 33.2 | 8.59 | 10.0 | 10.93 | 17.7 |
| 9.55 | 27.1 | 11.44 | 22.7 | 12.22 | 37.9 | 11.31 | 86.2 | 11.84 | 79.2 | 11.96 | 23.7 |
| 10.64 | 62.7 | 12.26 | 40.3 | 12.64 | 5.7 | 11.57 | 57.2 | 12.25 | 40.6 | 13.13 | 6.0 |
| 11.60 | 11.0 | 12.25 | 14.0 | 13.40 | 11.7 | 12.20 | 41.9 | 13.26 | 17.4 | 16.43 | 100.0 |
| 12.90 | 20.8 | 12.72 | 13.5 | 14.10 | 11.5 | 12.62 | 5.9 | 13.80 | 10.0 | 18.20 | 28.1 |
| 13.33 | 17.7 | 13.10 | 28.1 | 15.24 | 25.4 | 14.00 | 6.5 | 16.48 | 39.1 | 20.38 | 16.5 |
| 14.09 | 11.0 | 13.81 | 12.9 | 16.64 | 16.1 | 14.40 | 9.3 | 17.38 | 100.0 | 21.74 | 9.7 |
| 16.06 | 100.0 | 14.09 | 7.5 | 18.07 | 10.1 | 14.95 | 10.1 | 18.35 | 24.8 | 23.13 | 18.7 |
| 16.69 | 12.6 | 14.61 | 11.3 | 19.67 | 23.1 | 15.55 | 10.4 | 18.81 | 9.8 | 25.06 | 36.7 |
| 17.19 | 18.6 | 15.15 | 30.7 | 19.98 | 13.1 | 15.91 | 36.7 | 19.46 | 15.6 | 25.56 | 8.0 |
| 17.90 | 11.0 | 16.07 | 21.9 | 20.36 | 6.2 | 16.52 | 36.2 | 22.04 | 12.9 | 26.22 | 29.8 |
| 19.36 | 14.2 | 16.70 | 6.0 | 21.98 | 24.1 | 17.38 | 37.7 | 23.19 | 20.8 | 27.60 | 8.1 |
| 19.74 | 19.6 | 17.23 | 32.1 | 22.65 | 15.9 | 17.95 | 27.1 | 23.40 | 24.0 | 28.05 | 9.4 |
| 21.94 | 34.7 | 17.58 | 19.2 | 24.14 | 70.7 | 19.25 | 28.6 | 23.74 | 63.3 | 30.12 | 31.8 |
| 22.16 | 31.9 | 18.03 | 12.1 | 24.83 | 35.6 | 19.94 | 37.8 | 24.49 | 9.0 | 30.92 | 6.1 |

TABLE 1-continued

XRPD data of six kinds of leonurine crystals:

| Crystal form A | | Crystal form B | | Crystal form C | | Crystal form D | | Crystal form E | | Crystal form F | |
|---|---|---|---|---|---|---|---|---|---|---|---|
| 2-Theta | Relative intensity (%) | 2-Theta | Relative intensity (%) | 2-Theta | Relative intensity (%) | 2-Theta | Relative intensity (%) | 2-Theta | Relative intensity (%) | 2-Theta | Relative intensity (%) |
| 23.33 | 12.6 | 18.43 | 52.5 | 25.71 | 22.5 | 20.76 | 38.7 | 25.53 | 26.9 | 31.11 | 6.8 |
| 24.27 | 74.4 | 19.33 | 8.2 | 26.24 | 8.6 | 21.22 | 26.2 | 27.33 | 11.9 | 32.73 | 6.0 |
| 25.62 | 86.4 | 20.04 | 16.8 | 27.01 | 9.0 | 21.51 | 9.9 | 27.68 | 10.6 | 33.18 | 7.7 |
| 26.46 | 10.7 | 20.67 | 48.3 | 27.32 | 8.9 | 21.97 | 100.0 | 28.08 | 7.7 | 35.37 | 13.0 |
| 26.77 | 30.6 | 21.75 | 20.1 | 30.78 | 6.2 | 22.40 | 5.9 | 28.71 | 8.2 | 36.87 | 4.8 |
| 29.68 | 10.4 | 22.07 | 7.0 | 31.30 | 6.7 | 22.54 | 9.0 | 29.21 | 20.3 | 38.15 | 6.9 |
| 31.28 | 8.8 | 22.61 | 45.5 | 32.66 | 4.5 | 23.05 | 68.8 | 30.64 | 11.6 | 38.93 | 13.2 |
| 35.45 | 9.8 | 23.09 | 29.5 | 36.68 | 7.4 | 23.66 | 24.4 | 31.19 | 9.2 | | |
| 36.95 | 9.1 | 23.58 | 51.7 | | | 24.09 | 30.9 | 33.39 | 7.7 | | |
| 38.02 | 8.2 | 23.81 | 8.6 | | | 24.61 | 8.7 | 33.99 | 6.9 | | |
| | | 24.84 | 37.0 | | | 25.03 | 7.1 | | | | |
| | | 25.04 | 72.3 | | | 25.46 | 10.4 | | | | |
| | | 25.73 | 100.0 | | | 26.16 | 35.3 | | | | |
| | | 26.70 | 27.9 | | | 26.74 | 5.0 | | | | |
| | | 30.50 | 27.6 | | | 27.03 | 32.9 | | | | |
| | | 30.92 | 7.5 | | | 28.10 | 18.2 | | | | |
| | | 32.13 | 6.4 | | | 30.56 | 7.6 | | | | |
| | | 33.48 | 5.7 | | | 31.02 | 9.8 | | | | |
| | | 34.39 | 5.7 | | | 32.43 | 7.6 | | | | |
| | | 34.99 | 11.9 | | | 33.16 | 4.2 | | | | |
| | | 35.14 | 7.8 | | | 36.62 | 3.8 | | | | |
| | | 36.81 | 5.5 | | | 37.84 | 5.0 | | | | |
| | | 37.91 | 5.7 | | | 38.27 | 4.2 | | | | |
| | | 39.28 | 4.7 | | | 38.91 | 3.7 | | | | |

In the invention, the 6 kinds of leonurine crystal form described refer to the crystal with above-mentioned XRPD characteristics.

The invention provides an application of the drugs for insulin resistance syndrome prepared by the above-mentioned leonurine crystal.

More specifically, the invention provides a new insulin sensitizer, which contains the monomer active ingredient leonurin crystal separated and purified from the Chinese Motherwort. The insulin sensitizer is suitable for the treatment of various diseases caused by the decrease of insulin sensitivity, especially as a hypoglycemic agent for the treatment of diabetes, and can also be used to treat insulin resistance syndrome.

The leonurine crystal of the invention is also applicable to treat the secondary disease caused by insulin resistance syndrome in the precision medical practice, including but not limited to hyperglycemia, hyperlipidemia, obesity, hypertension and other diseases. In the implementation of the invention, the treatment of diseases caused by the reduction of insulin sensitivity in the above-mentioned diseases is individualized.

Leonurine crystal of the invention could be used as pharmaceutical raw materials, which usually used to prepare suitable medicine including capsules, tablets, powders, suspensions and compound preparations directly or by mixing with other solid or liquid auxiliary materials.

The invention has been studied pharmacologically. The results showed that leonurine crystal can enhance the insulin sensitivity of the body, the body's response to insulin, the physiological effect of insulin and the sensitivity of the insulin receptor; which could be used as insulin sensitizer to treat insulin resistance syndrome and the secondary disease caused by insulin resistance syndrome, including but not limited to hyperglycemia, hyperlipidemia, obesity, hyperviscosity, hypertension, etc. The leonurine crystal described in the invention has the effect of reducing blood glucose and blood lipids, and can also be used to treat diabetes and hyperlipidemia, as well as secondary atherosclerosis. The leonurine crystal described in the invention also has the effect of reducing body weight and can be used to treat simple obesity; the leonurine crystal has the effect of increasing insulin receptor sensitivity and can be used as insulin sensitizer to treat insulin resistance syndrome.

In the invention, the experiment of preparing and identifying leonurine crystal was carried out;

Crystal Screening Method:

The crystal form of leonurine was screened and prepared by experimental procedures or methods, such as suspension crystallization, volatile crystallization, cooling crystallization, anti-solvent crystallization, phase transition during heating and cooling, water adsorption and desorption experiments, etc.

In the invention, the methods for studying and identifying the obtained leonurine crystal include:

Thermogravimetic analysis (TGA) method, instrument model: Netzsch TG 209F3, temperature range: 30-400° C., scanning rate: 10° C./min, sweeping gas: 25 mL/min, shielding gas: 15 mL/min;

Differential scanning calorimetry (DSC) method, instrument model: Perkin Elmer DSC 8500, temperature range: 50-230° C., scanning rate:10° C./min, the flow rate of nitrogen: 50 mL/min;

X-ray powder diffraction (XRPD) method, instrument model: Bruker D8 advance, target: Cu Kα(40 kV, 40 mA), Sample to detector distance: 30 cm, scanning range: 3°-40° (2 theta value), scanning step: 0.05 s;

Dynamic vapor sorption (DVS) method, instrument model: SMS DVS Intrinsic, 0~95% RH, temperature: 25° C.; FTIR method, instrument model: Nicolet 6700, sectral range: 4000~400 $cm^{-1}$, resolution ratio: 4 $cm^{-1}$, scanning times: 32, the infrared spectra of the samples were determined by KBr pressed-disk technique method, temperature: 25° C.;

Thermal weightlessness analysis (TGA), Raman spectroscopy (Raman), infrared spectroscopy (IR), etc.

In the invention, the dominant medicinal crystal form was also screened by the accelerated stability experimental method, and observed the transformation among the various crystal forms.

Through the above methods, 6 kinds of leonurine crystal form, that is, above-mentioned crystal form A, B, C, D, E and F, were screened and identified, in which the crystal form A is the dominant medicinal crystal form.

The invention carries out insulin sensitization experiment of leonurine crystal form A:

After the rats were given different doses of the above leonurine crystal form A, the insulin sensitivity of rats was measured, the curve of insulin sensitivity was made, and the effect of leonurine crystal form A on the curve of insulin sensitivity was observed and compared to the control group. The results showed that the leonurine crystal form A could cause the curve of insulin sensitivity to move down and left. Compared with the control group, leonurine crystal form A increased the insulin sensitivity of rats, and the difference was statistically significant;

The experiment results of the invention also indicated that because insulin produces physiological effects through insulin receptors, leonurine crystal form A increase the body's sensitivity to insulin. It is further shown that the target of leonurine crystal form A is in the insulin receptor or its coupled signaling pathways.

The invention provides the use of leonurine crystal form A extracted from chinese herbal medicine, the Chinese Motherwort, in the preparation of insulin sensitizer. The above-mentioned insulin sensitizer is especially suitable for secondary diseases caused by the treatment of insulin resistance syndrome and the decrease of insulin sensitivity, including but not limited to hyperglycemia, hyperlipidemia, obesity, hyperviscosity, hypertension, etc.

The invention also carried out the experiment of leonurine crystal form A for the treatment of lipid-lowering and atherosclerosis:

The animal model of hyperlipidemia was created by giving a high-fat diet to the ApoE gene knockout mice. In this model, the leonurine crystal form A was given to observe the effect on various indexes of lipid metabolism, and compared with the effect of positive drug Atorvastatin. The experiment results showed that the leonurine crystal form A could significantly decrease the concentration of total cholesterol, triglycerides and low-density lipoprotein in the serum of above animals;

The invention also studies the lipid-lowering effect of the leonurine crystal form A in the atherosclerosis model of New Zealand white rabbit fed with high cholesterol. The experiment showed that intragastric administration of different doses of leonurine crystal form A to high-fat rabbits, which can decrease the concentration of total cholesterol and triglycerides in the serum;

In the model of rhesus monkey with hyperlipidemia, long-term administration of leonurine crystal form A showed the effect of decreasing total cholesterol (TC) and low-density lipoprotein (LDL-C).

The invention provides a new structure of leonurine crystal form and the new application of its dominant medicinal crystal form in the preparation of drugs; the related leonurine crystal form can be used to prepare insulin sensitizer and lipid metabolic disorder regulator.

NC, normal diet group; MD, atherosclerotic model group; ST, Atorvastatin group; AS, aspirin group; SCM198-L, low dose group of leonurine crystal form A; SCM198-M, medium dose group of leonurine crystal form A; SCM198-H, high dose group of leonurine crystal form A; the white ruler represents 1 mm.

Figure 30:
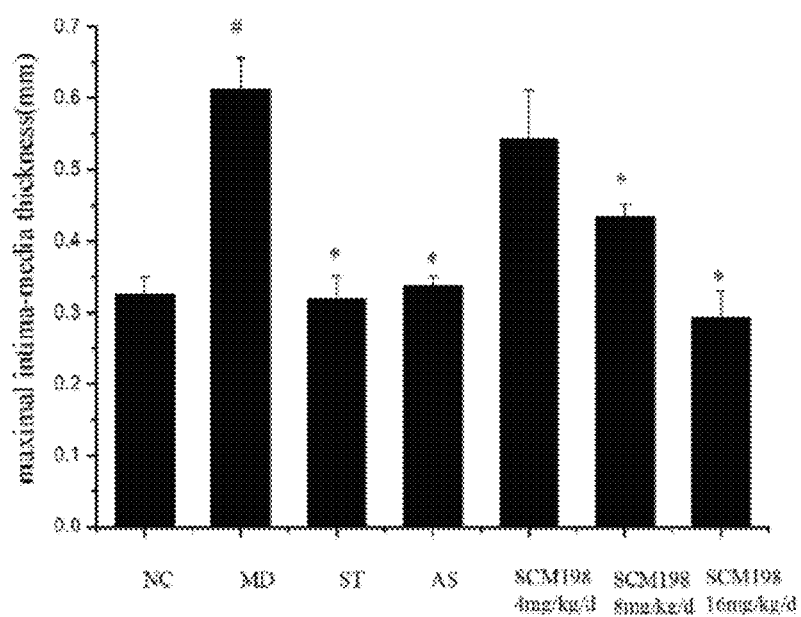

FIG. 30 is a statistical comparison diagram of intimal-medial thickness (IMT) data at the largest plaque of carotid atheromatous plaque in the micro-ultrasonic end-diastole. The plaque thickness of model group was significantly thickened, and medium and high dose group of leonurine crystal form A could decrease plaque thickness;

NC, normal diet group; MD, atherosclerotic model group; ST, Atorvastatin group; AS, aspirin group; SCM198 4 mg/kg/d, low dose group of leonurine crystal form A; SCM198 8 mg/kg/d, medium dose group of leonurine crystal form A; SCM198 16 mg/kg/d, high dose group of leonurine crystal form A; #P<0.01, compared with the normal group; *P<0.05, compared with the model group.

DETAILED DESCRIPTION OF THE INVENTION

The following examples illustrate more specifically the preparation, method for the identification of Leonurine Crystal, drug-delivery way, forms of preparation, operating conditions and the order, as shown in this invention and examples can be changed appropriately within the limits of the spirit of the invention.

EXAMPLE 1

Preparation of Leonurine Crystal by Suspension Crystallization

Take about 20 g leonurine sulfate raw material medicine, mix with 1 mL solvent respectively under the condition of 25° C. and 50° C. for at least 24 h, then filter solution separately, the solid part is dried in air for 10 min, and subsequently taking an X-ray powder diffraction (XRPD) detection. If it is observed that the measured XRPD spectrogram is different from the raw material spectrogram, further measurements are conducted (such as DSC, TGA, IR, DVS, etc.). The liquid part is volatilized in a vacuum to determination of approximate solubility of raw material medicine in solvents by gravimetric analysis. XRPD detection was conducted for the solid precipitated after solvent volatilization. If it is observed that the measured XRPD spectrogram is different from the raw material spectrogram, further measurements are conducted (such as DSC, TGA, IR, DVS, etc.).

Gravimetric analysis method: Accurately take the filtrate of a certain volume (usually 0.5 mL) and put it into a dry and weighed container, recorded as M0 mg, weigh the total weight accurately after volatilizing the solvent in a vacuum, recorded as M1 mg. Then the mass of the precipitated solid is M1-M1, the volume of the solvent is V mL, according to this, the approximate solubility of the raw material in the solvent is X=(M1-M0)/V mg/mL.

Table 2 shows the results of suspension crystallization in solvent under the condition of 50° C.

TABLE 2 the results of suspension crystallization
in solvent under the condition of 50° C.

Figure 1:
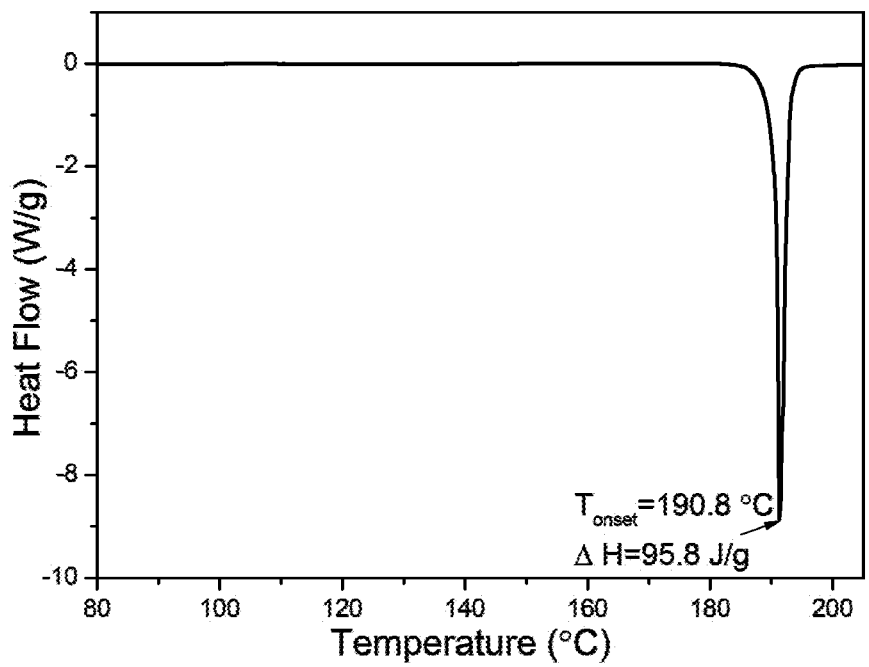
FIG. 1 is a differential scanning calorimetry (DSC) diagram of crystal form B.
Figure 2:
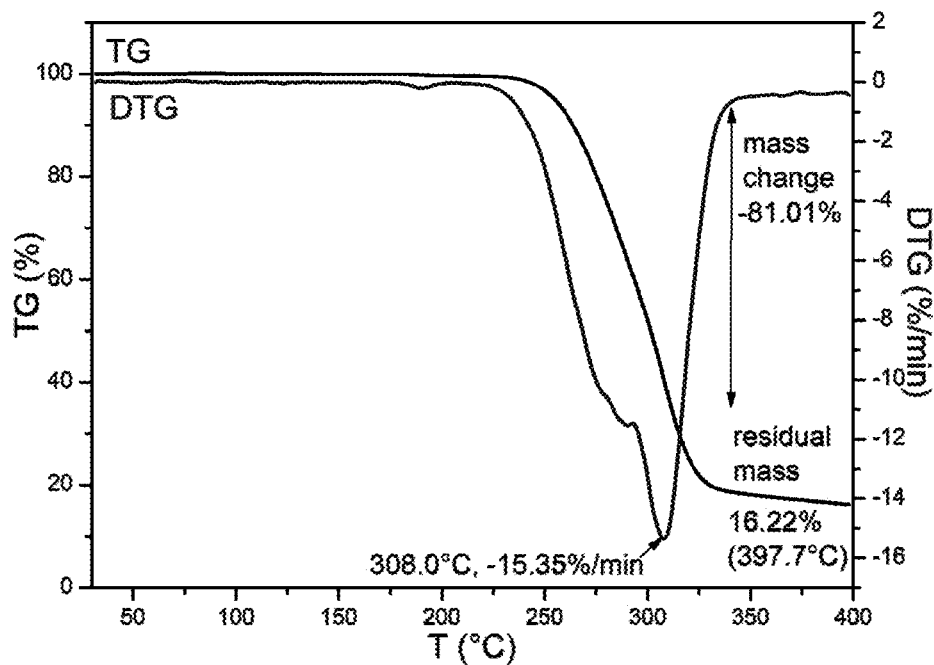
FIG. 2 is a thermogravimetric analysis (TGA) diagram of crystal form B.
Figure 3:
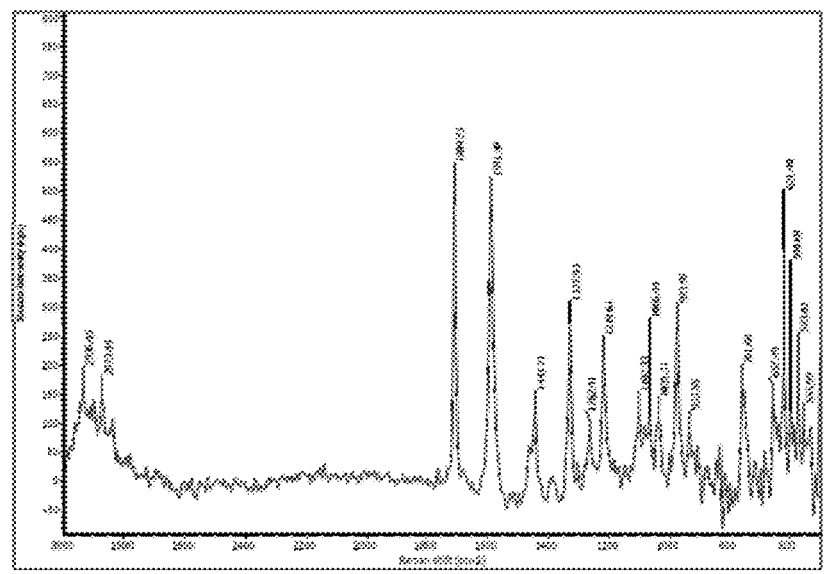
FIG. 3 is a Raman spectra (Raman) diagram of crystal form B.
Figure 7:
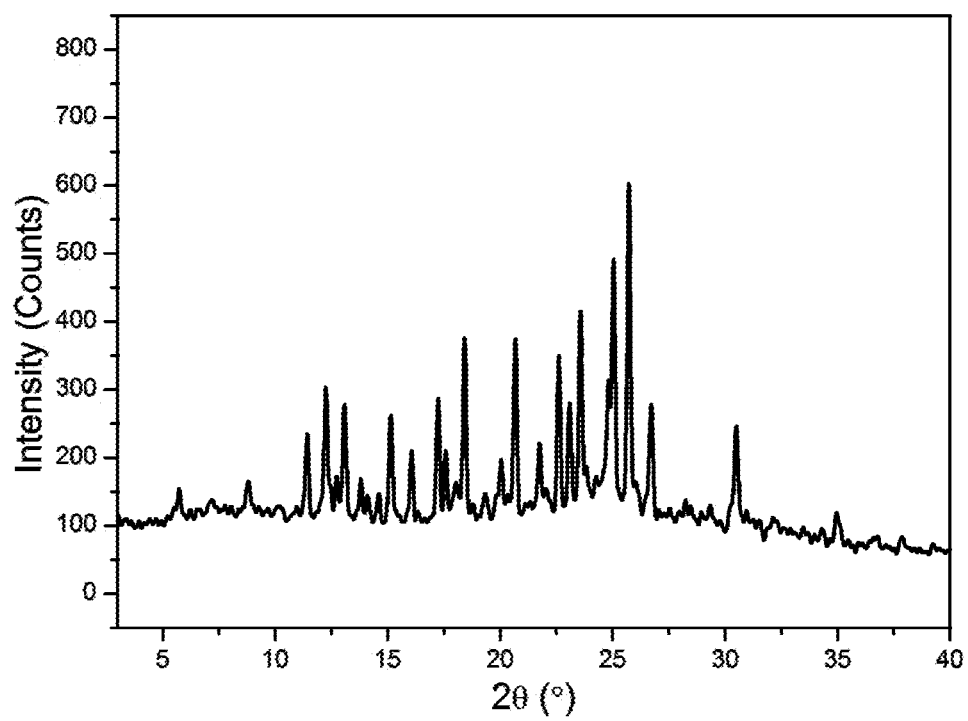
FIG. 7 is an XRPD diagram of crystal form B.

| Solvent | XRPD | DSC | TGA | Raman |
|---|---|---|---|---|
| Methanol | — | — | — | — |
| Ethanol | — | — | — | — |
| Isopropanol | Crystal Form B (FIG. 7) | FIG. 1 | FIG. 2 | FIG. 3 |
| Acetone | — | — | — | — |
| Methyl ethyl ketone | — | — | — | — |
| Acetonitrile | Crystal Form B (FIG. 7) | FIG. 1 | FIG. 2 | FIG. 3 |
| Tetrahydrofuran | Crystal Form B (FIG. 7) | FIG. 1 | FIG. 2 | FIG. 3 |
| Nitromethane | Crystal Form B (FIG. 7) | FIG. 1 | FIG. 2 | FIG. 3 |
| Ethyl acetate | Crystal Form B (FIG. 7) | FIG. 1 | FIG. 2 | FIG. 3 |
| Isopropyl acetate | — | — | — | — |
| Isoamyl alcohol | Crystal Form B (FIG. 7) | FIG. 1 | FIG. 2 | FIG. 3 |
| Methyl t-butyl ether | — | — | — | — |
| Toluene | — | — | — | — |
| Methyl isobutyl ketone | Crystal Form B (FIG. 7) | FIG. 1 | FIG. 2 | FIG. 3 |
| Hexane | — | — | — | — |
| Heptane | — | — | — | — |
| Diethyl ether | — | — | — | — |
| Dichloromethane | Crystal Form B (FIG. 7) | FIG. 1 | FIG. 2 | FIG. 3 |
| Chloroform | — | — | — | — |
| Petroleum ether | — | — | — | — |
| Water | — | — | — | — | where, (1) Using "-" to indicate that no change has been detected compared to the raw material. (2) If it detects any changes compared to raw materials, using the DSC mark the Onset temperature, the TGA mark the weightlessness temperature and its percentage, and mark the corresponding spectrogram number respectively.

The leonurine crystal form B with XRPD data characteristics as shown in Table 1 was obtained by the above method especially the solvent combination, the DSC, TGA and Raman spectral data characteristics are shown in FIG. 1, FIG. 2 and FIG. 3 respectively; The above data provides the basis for the identification of the leonurine crystal form B.

EXAMPLE 2

Preparation of Leonurine Crystal by Evaporative Crystallization

Prepare 2 groups of leonurine sulfate samples, each group weighed 96 parts, about 3 mg per part, add solvent according to the design shown in Table 3, mix, and dissolve. Slowly volatilize to dry under the condition of 25° C. and 50° C. respectively (this process will take 24 h to several days), then collect solids, test and analyze XRPD, DSC, TGA and Raman spectroscopy. The aforementioned suspension experiments are used for the insoluble ones under this condition.

TABLE 3

Slow volatile solvent table (showing the solvent combination scheme for the preparation of leonurine crystal by evaporative crystallization)

| | 1 | 2 | 3 | 4 | 5 | 6 | 7 | 8 | 9 | 10 | 11 | 12 |
|---|---|---|---|---|---|---|---|---|---|---|---|---|
| A | 400 ul MeOH | 400 ul EtOH | 400 ul i-PrOH | 400 ul IAA | 400 ul Acetone | 400 ul MEK | 400 ul ACN | 400 ul THF | 400 ul NM | 400 ul EA | 400 ul MTBE | 400 ul Toluene |
| B | 400 ul MeOH 200 ul H$_2$O | 400 ul EtOH 200 ul H$_2$O | 400 ul i-PrOH 200 ul H$_2$O | 400 ul IAA 200 ul H$_2$O | 400 ul Acetone 200 ul H$_2$O | 400 ul MEK 200 ul H$_2$O | 400 ul ACN 200 ul H$_2$O | 400 ul THF 200 ul H$_2$O | 400 ul NM 200 ul H$_2$O | 400 ul EA 200 ul H$_2$O 200 ul MeOH | 200 ul MTBE 200 ul H$_2$O 200 ul MeOH | 400 ul Toluene 200 ul H$_2$O 200 ul MeOH |
| C | 400 ul MeOH 400 ul H$_2$O | 400 ul EtOH 400 ul H$_2$O | 400 ul i-PrOH 400 ul H$_2$O | 400 ul IAA 400 ul H$_2$O | 400 ul Acetone 400 ul H$_2$O | 400 ul MEK 400 ul H$_2$O | 400 ul ACN 400 ul H$_2$O | 400 ul THF 400 ul H$_2$O | 400 ul NM 400 ul H$_2$O | 400 ul EA 400 ul H$_2$O 200 ul MeOH | 400 ul MTBE 400 ul H$_2$O 200 ul MeOH | 400 ul Toluene 400 ul H$_2$O 200 ul MeOH |
| D | 400 ul MeOH 400 ul Hex | 400 ul EtOH 400 ul Hex | 400 ul i-PrOH 400 ul Hex | 400 ul IAA 400 ul Hex | 400 ul Acetone 400 ul Hex | 400 ul MEK 400 ul Hex | 400 ul ACN 400 ul Hex | 400 ul THF 400 ul Hex | 400 ul NM 400 ul Hex | 400 ul EA 400 ul Hex | 400 ul MTBE 400 ul Hex | 400 ul Toluene 400 ul Hex |
| E | 400 ul MeOH 400 ul Hep | 400 ul EtOH 400 ul Hep | 400 ul i-PrOH 400 ul Hep | 400 ul IAA 400 ul Hep | 400 ul Acetone 400 ul Hep | 400 ul MEK 400 ul Hep | 400 ul ACN 400 ul Hep | 400 ul THF 400 ul Hep | 400 ul NM 400 ul Hep | 400 ul EA 400 ul Hep | 400 ul MTBE 400 ul Hep | 400 ul Toluene 400 ul Hep |
| F | 400 ul MeOH 400 ul MTBE | 400 ul EtOH 400 ul MTBE | 400 ul i-PrOH 400 ul MTBE | 400 ul IAA 400 ul MTBE | 400 ul Acetone 400 ul MTBE | 400 ul MEK 400 ul MTBE | 400 ul ACN 400 ul MTBE | 400 ul THF 400 ul MTBE | 400 ul NM 400 ul MTBE | 400 ul EA 400 ul MTBE | 400 ul MTBE 200 ul MeOH | 400 ul Toluene 200 ul MeOH |
| G | 400 ul MeOH 400 ul Toluene | 400 ul EtOH 400 ul Toluene | 400 ul i-PrOH 400 ul Toluene | 400 ul IAA 400 ul Toluene | 400 ul Acetone 400 ul Toluene | 400 ul MEK 400 ul Toluene | 400 ul ACN 400 ul Toluene | 400 ul THF 400 ul Toluene | 400 ul NM 400 ul Toluene | 400 ul EA 400 ul Toluene | 400 ul MTBE 200 ul EtOH | 400 ul Toluene 200 ul EtOH |

TABLE 3-continued

Slow volatile solvent table (showing the solvent combination scheme for the preparation of leonurine crystal by evaporative crystallization)

| | 1 | 2 | 3 | 4 | 5 | 6 | 7 | 8 | 9 | 10 | 11 | 12 |
|---|---|---|---|---|---|---|---|---|---|---|---|---|
| H | 400 ul MeOH 400 ul MIBK | 400 ul EtOH 400 ul MIBK | 400 ul i-PrOH 400 ul MIBK | 400 ul IAA 400 ul MIBK | 400 ul Acetone 400 ul MIBK | 400 ul MEK 400 ul MIBK | 400 ul ACN 400 ul MIBK | 400 ul THF 400 ul MIBK | 400 ul NM 400 ul MIBK | 400 ul EA 400 ul MIBK | 400 ul MTBE 400 ul MIBK | 400 ul Toluene 200 ul MIBK |

Where, MeOH=Methanol; EtOH=Ethanol; i-PrOH=Isopropanol; IAA=Isoamyl alcohol; MEK=Methyl ethyl ketone; ACN=Acetonitrile; MTBE=Methyl tert-butyl ether; MIBK=Methyl isobutyl ketone; NM=Nitromethane; THF=Tetrahydrofuran; EA=Ethyl acetate; Hep=N-heptane; Hex=Hexane Experimental result: According to the solvent combination scheme shown in Table 3, after the solvent is volatilized, several kinds of leonurine crystals as shown in Table 4 below can be obtained.

TABLE 4

Experiment results of slow solvent evaporation crystallization at 25° C. obtained according to the solvent combination scheme shown in Table 3.

Figure 4:
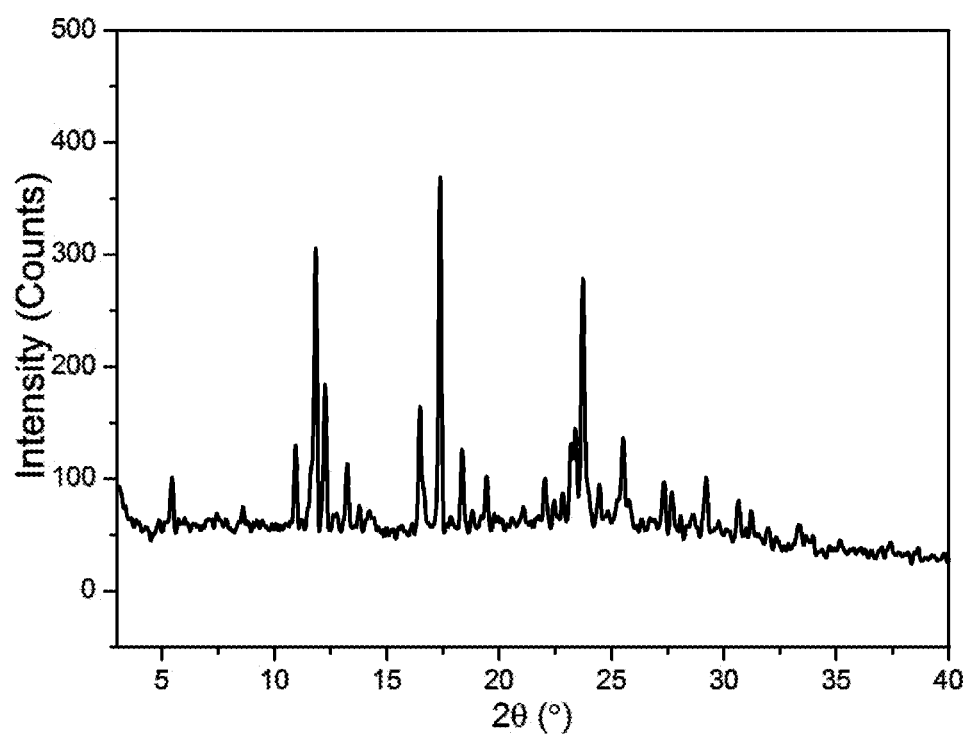
FIG. 4 is an XRPD diagram of leonurine crystal form E.

| | 1 | 2 | 3 | 4 | 5 | 6 | 7 | 8 | 9 | 10 | 11 | 12 |
|---|---|---|---|---|---|---|---|---|---|---|---|---|
| A | — | — | — | — | | | | — | | — | — | — |
| B | — | — | Crystal Form E (FIG. 4) | — | | — | — | Crystal Form E (FIG. 4) | | — | — | |
| C | — | — | Crystal Form E (FIG. 4) | Crystal Form E (FIG. 4) | — | — | — | — | | | — | — |
| D | | | | | | — | | | | | | |
| E | | | | | | | | | | | | |
| F | | | | | | | | | | | | |
| G | | | | | | | | | | | | |
| H | | | | Powder volatilization disappeared and could not be determined | | | | | | | | |

Where, (1) Using "—" to indicate that no crystal form changes have been detected compared to leonurine sulfate raw material. (2) If it's detected that there are any changes in the crystal form compared with leonurine sulfate raw material, the number of corresponding XRPD spectrogram is shown in parentheses. (3) The blank indicates that suspension crystallization are made because the sample cannot be dissolved.

As shown in Table 4, according to the solvent combination scheme listed in Table 3, the solvents slowly volatile under the condition of 25° C., and the crystal form E of the leonurine can be obtained in four solvent combination schemes. This crystal has the XRPD spectrogram features shown in Table 1 and FIG. 4.

Figure 5:
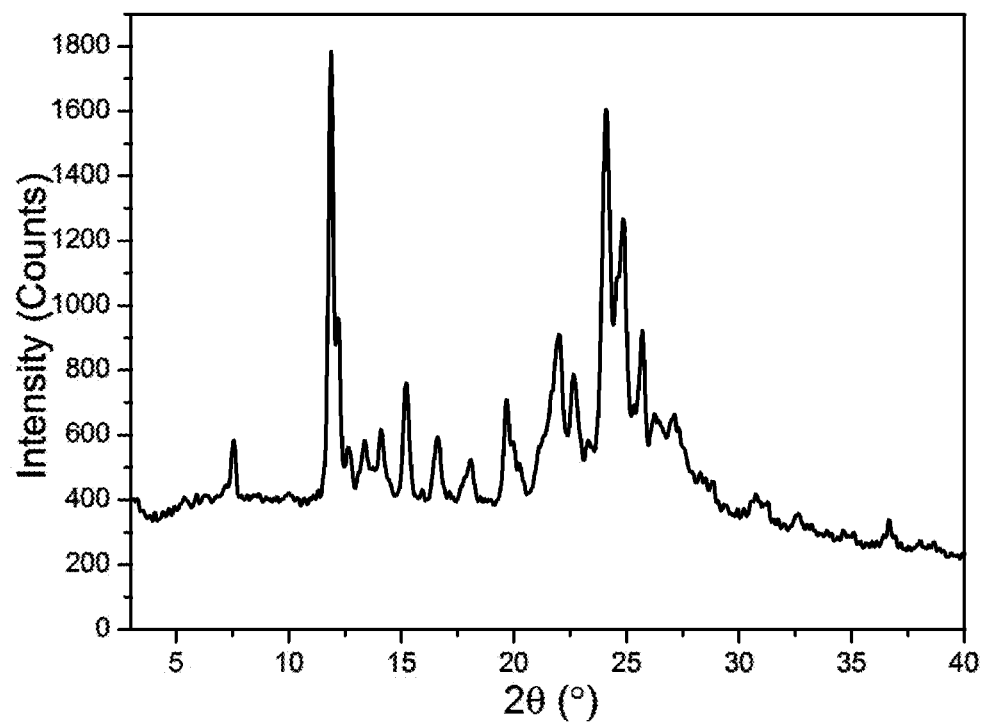
FIG. 5 is an XRPD diagram of crystal form C.
Figure 6:
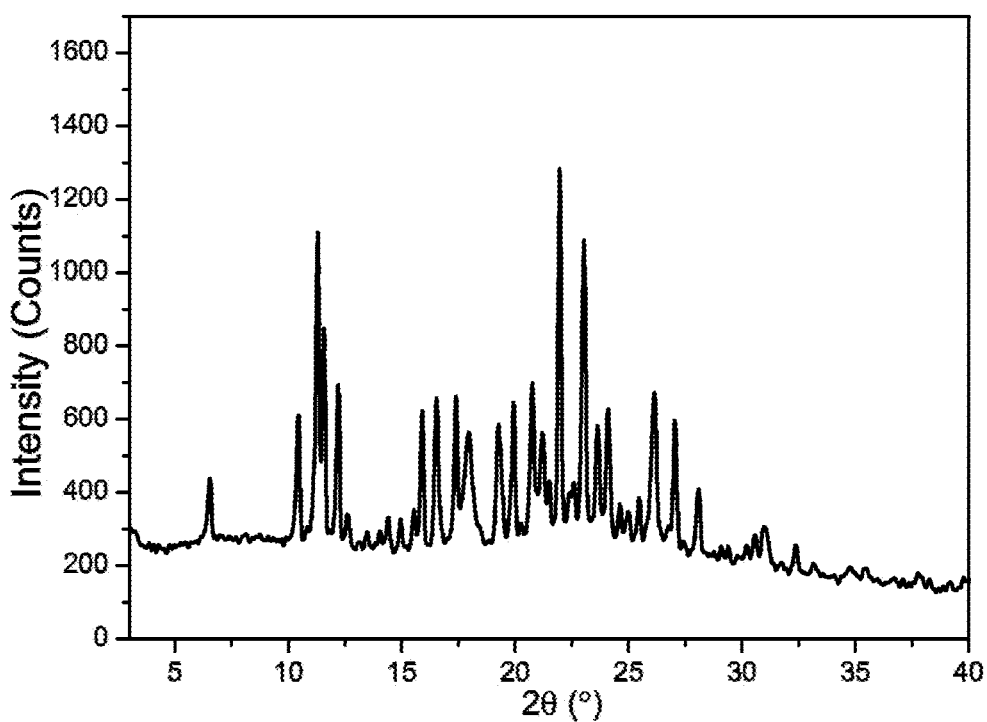
FIG. 6 is an XRPD diagram of crystal form D.

According to the solvent combination scheme shown in table 3, suspension crystallization is used for samples that cannot be dissolved, and the results are shown in Table 5, crystal form C and crystal form D can be obtained by suspension crystallization test; The XRPD data for identifying crystal form C is shown in Table 1, and the spectrogram is shown in FIG. 5; The XRPD data for identifying crystal form D is shown in Table 1, and the spectrogram is shown in FIG. 6.

TABLE 5

Experiment results of suspension at 25° C. obtained according to the solvent combination scheme shown in Table 3.

| | 1 | 2 | 3 | 4 | 5 | 6 | 7 | 8 | 9 | 10 | 11 | 12 |
|---|---|---|---|---|---|---|---|---|---|---|---|---|
| A | — | — | | | — | — | — | — | — | — | — | — |
| B | | | | | | — | | | — | | | — |
| C | | | | | | | | | — | | | — |
| D | Crystal Form C (FIG. 5) | Crystal Form D (FIG. 6) | — | — | — | | — | — | — | — | — | — |

TABLE 5-continued

Experiment results of suspension at 25° C. obtained according to the solvent combination scheme shown in Table 3.

|   | 1 | 2 | 3 | 4 | 5 | 6 | 7 | 8 | 9 | 10 | 11 | 12 |
|---|---|---|---|---|---|---|---|---|---|---|---|---|
| E | Crystal Form C (FIG. 5) | Crystal Form D (FIG. 6) | — | — | — | — | — | — | — | — | — | — |
| F | Crystal Form C (FIG. 5) | — | — | — | — | — | — | — | — | — | Crystal Form C (FIG. 5) | Crystal Form C (FIG. 5) |
| G | Crystal Form C (FIG. 5) | — | — | — | — | — | — | — | — | — | — | — |
| H | Crystal Form C (FIG. 5) | — | — | — | — | — | — | — | — | — | — | — | where, (1) Using "-" to indicate that there is no change have been detected compared to leonurine sulfate raw materials. (2) If it detects any changes compared to raw materials, identify the crystal form and mark its XRPD spectrogram number in parentheses. (3) The blank indicates that evaporative crystallization are made because the sample can be dissolved.

In this example, by designing different solvent combination schemes, after eliminating the solvent combination scheme that does not produce new crystal form (as compared to the synthesized leonurine sulfate raw material medicine), the leonurine crystal are prepared by evaporative crystallization in a soluble solvent combination scheme to obtain leonurine crystal form E. In the samples that could not be dissolved, the suspension crystallization was used for obtaining the leonurine crystal form C and D. In this example, the identification of different leonurine crystal forms is based on XRPD data and spectrogram. The solvent slow evaporation crystallization experiment was repeated according to the solvent combination scheme shown in Table 3 under the condition of 50° C., and the sample in which the leonurine could not be dissolved was used as a suspension crystallization test. The experiment results show that according to the solvent combination scheme shown in Table 3, volatilize the solvent can obtain several kinds of leonurine crystals as shown in Table 6 below.

TABLE 6

Experiment results of slow solvent evaporation crystallization at 50° C. obtained according to the solvent combination scheme shown in Table 3.

|   | 1 | 2 | 3 | 4 | 5 | 6 | 7 | 8 | 9 | 10 | 11 | 12 |
|---|---|---|---|---|---|---|---|---|---|---|---|---|
| A | — | — | Crystal Form B (FIG. 4) | Crystal Form B (FIG. 7) | — | — | Crystal Form B (FIG. 7) | Crystal Form B (FIG. 7) | Crystal Form B (FIG. 7) | Crystal Form B (FIG. 7) | — | — |
| B | — | Crystal Form E (FIG. 4) | Crystal Form E (FIG. 4) | — | — | — | — | — | Crystal Form E (FIG. 4) | — | — | Crystal Form E (FIG. 4) |
| C | Crystal Form E (FIG. 4) | — | Crystal Form E (FIG. 4) | Crystal Form E (FIG. 4) | — | — | — | — | — | — | — | — |
| D | — | — | — | — |   |   |   |   |   |   |   |   |
| E |   |   |   |   |   |   |   |   |   |   |   |   |
| F |   |   |   |   |   |   |   |   |   |   |   |   |
| G |   |   |   |   |   |   |   |   |   |   |   |   |
| H |   |   |   |   |   |   |   |   |   |   |   |   |

Where, (1) Using "-" to indicate that there is no change have been detected compared to to the raw material. (2) If any change is detected compared to the raw material, mark the identified crystal form and mark its XRPD spectrogram number in parentheses. (3) The blank indicates that suspension crystallization are made because the leonurine sample cannot be dissolved.

In the experiment shown in Table 6, in which the leonurine sample could not be dissolved was continuously subjected to a suspension crystallization test under the condition of 50° C., and the results are shown in Table 7:

TABLE 7

Experiment results of suspension crystallization at 50° C. obtained according to the solvent combination scheme shown in Table 3.

| | 1 | 2 | 3 | 4 | 5 | 6 | 7 | 8 | 9 | 10 | 11 | 12 |
|---|---|---|---|---|---|---|---|---|---|---|---|---|
| A | | | | | | | | | | | | |
| B | | | | Crystal Form E (FIG. 4) | | | | | | | | |
| C | | | | | | | | | | | | |
| D | | | — | | | — | Crystal Form B (FIG. 7) | — | Crystal Form B (FIG. 7) | — | — | — |
| E | — | — | Crystal Form B (FIG. 7) | Crystal Form B (FIG. 7) | — | — | Crystal Form B (FIG. 7) | — | Crystal Form B (FIG. 7) | — | — | — |
| F | — | — | Crystal Form B (FIG. 7) | Crystal Form B (FIG. 7) | — | — | Crystal Form B (FIG. 7) | Crystal Form B (FIG. 7) | — | — | Crystal Form C (FIG. 5) | Crystal Form C (FIG. 5) |
| G | — | Crystal Form D (FIG. 6) | Crystal Form B (FIG. 7) | Crystal Form B (FIG. 7) | — | — | Crystal Form B (FIG. 7) | Crystal Form B (FIG. 7) | — | — | — | Crystal Form D (FIG. 6) |
| H | Crystal Form C (FIG. 5) | — | Crystal Form B (FIG. 7) | Crystal Form B (FIG. 7) | — | — | Crystal Form B (FIG. 7) | Crystal Form B (FIG. 7) | — | Crystal Form B (FIG. 7) | — | — |

Where, (1) Using "-" to indicate that no change has been detected compared to leonurine sulfate raw materials; (2) If any change is detected compared to leonurine sulfate raw materials, identify the crystal form and mark its XRPD spectrogram number in parentheses; (3) The blank indicates that evaporative crystallization is made because the sample can be dissolved.

The above experiment results show that under the condition of 50° C., according to the solvent combination scheme of Table 3, the combination of the crystal form of the leonurine is significantly different from that is obtained at 25° C. Specifically, the leonurine crystal form B and E were obtained in the volatile crystallization experiment (Table 6). In the suspension crystallization experiment, four crystal forms of leonurine were obtained, specifically crystal forms B, C, D and E (Table 7). Identification of all of the above-mentioned leonurine crystal form is based on the corresponding XRPD data and spectrogram shown.

EXAMPLE 3

Cooling Crystallization from Hot Concentrated Solution

About 6 mg leonurine sulfate raw material was taken and dissolved in solvent, heated to 60° C. until completely dissolved, then cooled to room temperature, filtered, measure the solid, or put it into the refrigerator at 4° C. until the crystals are precipitated.

TABLE 8

Cooling crystallization results in hot concentrated solution

Figure 8:
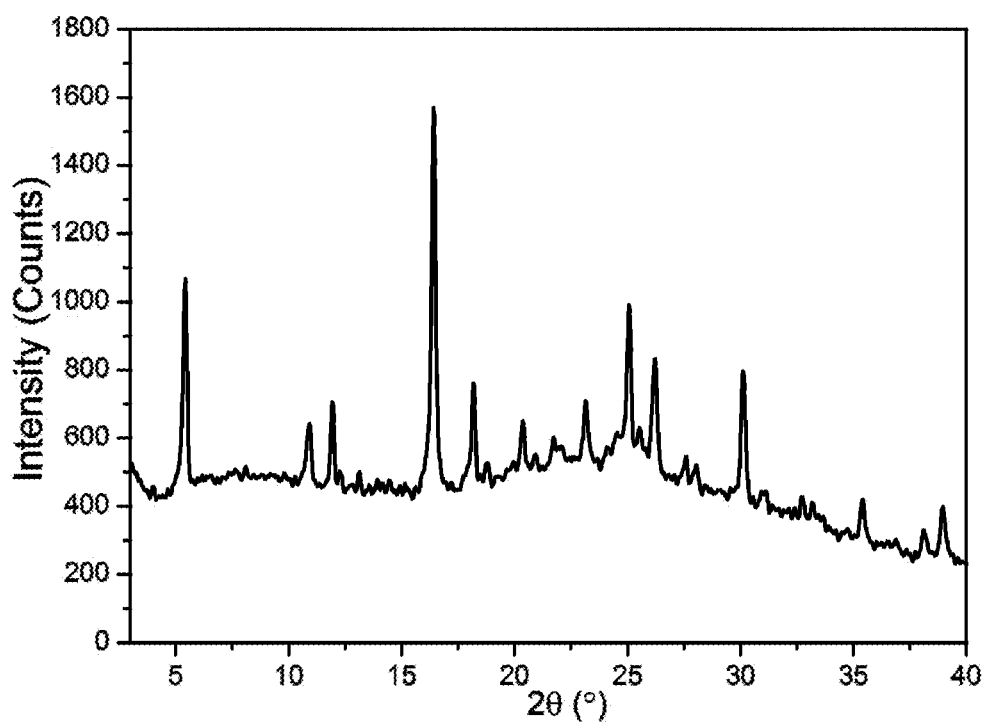
FIG. 8 is an XRPD diagram of crystal form F.
Figure 9:
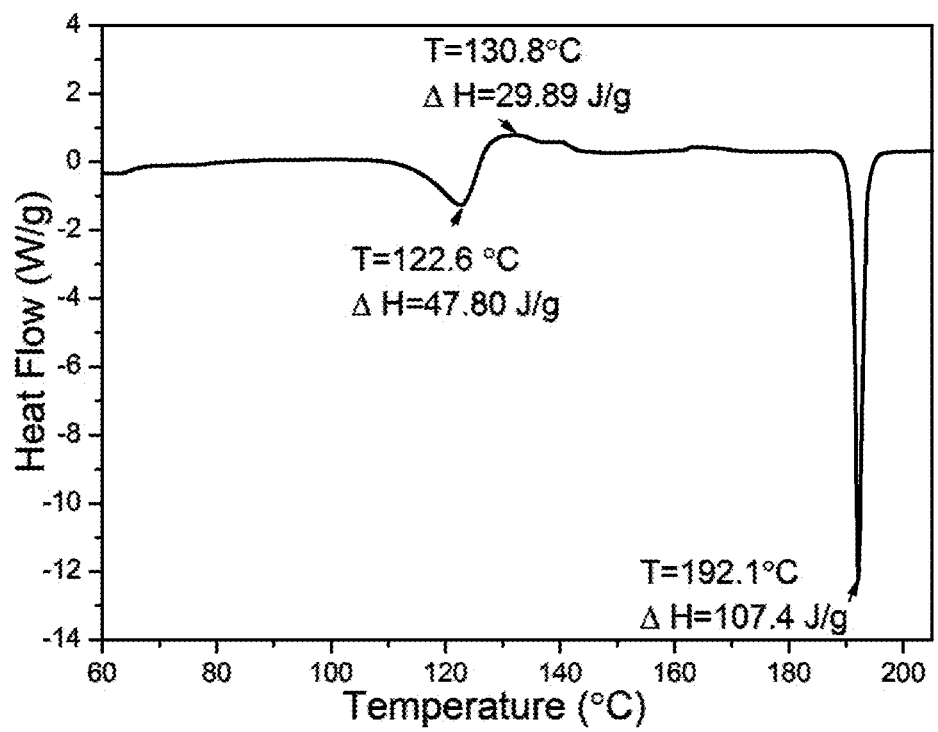
FIG. 9 is a differential scanning calorimetry (DSC) diagram of crystal form F.
Figure 10:
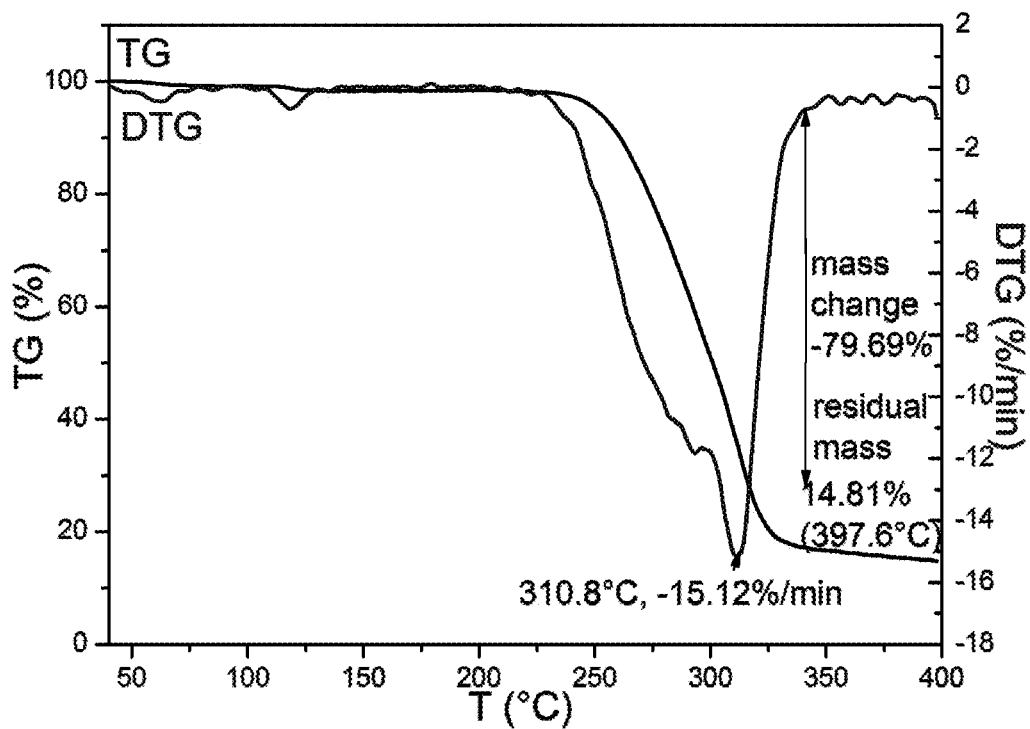
FIG. 10 is a thermogravimetric analysis (TGA) diagram of crystal form F.
Figure 11:
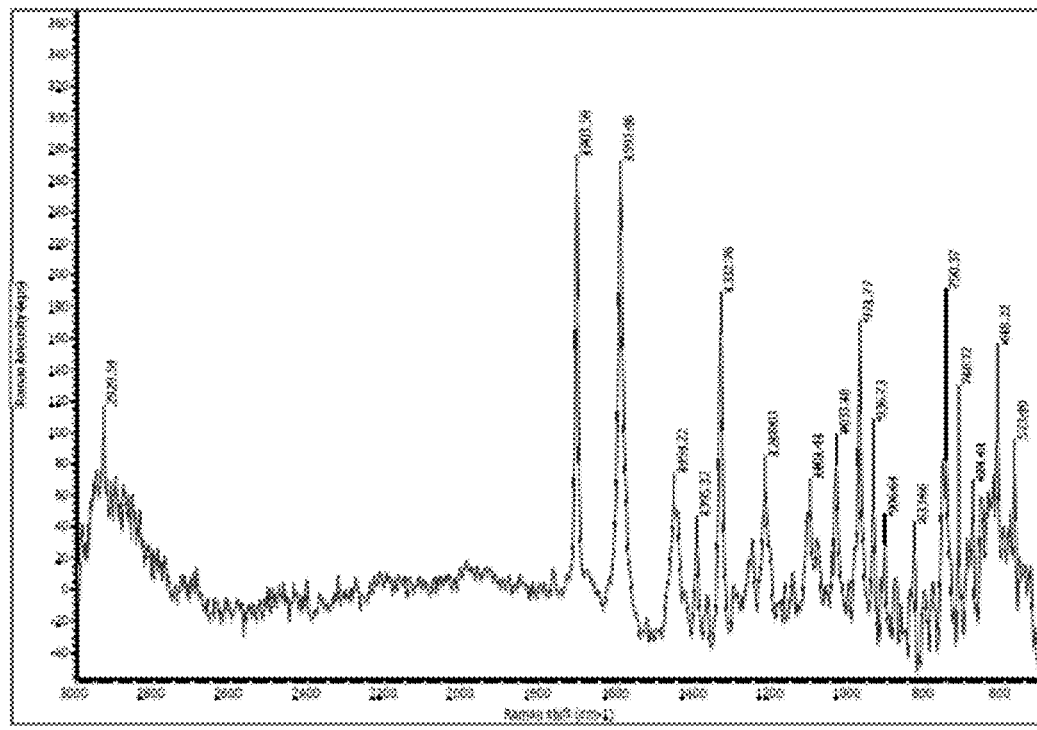
FIG. 11 is a Raman spectra (Raman) diagram of crystal form F.

| solvent | XRPD | DSC | TGA | Raman |
|---|---|---|---|---|
| MeOH | Crystal Form F (FIG. 8) | Crystal Form F (FIG. 9) | Crystal Form F (FIG. 10) | Crystal Form F (FIG. 11) |
| EtOH | — | — | — | — |
| CHCl₃ | — | — | — | — |
| MTBE | — | — | — | — |

Where, (1) Using "-" to indicate that no change has been detected compared to to the raw material of the leonurine sulfate; (2) If any changes is detected compared to leonurine sulfate raw materials, using XRPD, DSC, TGA and Raman to identify and mark the corresponding spectrogram number. The DSC marks the $T_{onset}$ temperature, and the TGA marks the starting weightlessness temperature;

Through the above experiments, the leonurine crystal form F was obtained by cooling crystallization in a hot solution of MeOH, and was determined by XRPD, DSC, TGA and Raman, confirmed as Form F. Identification of crystal form is based on the corresponding XRPD data and spectrogram.

EXAMPLE 4

Single Crystal Analysis of Leonurine Crystal Form A

Figure 12:
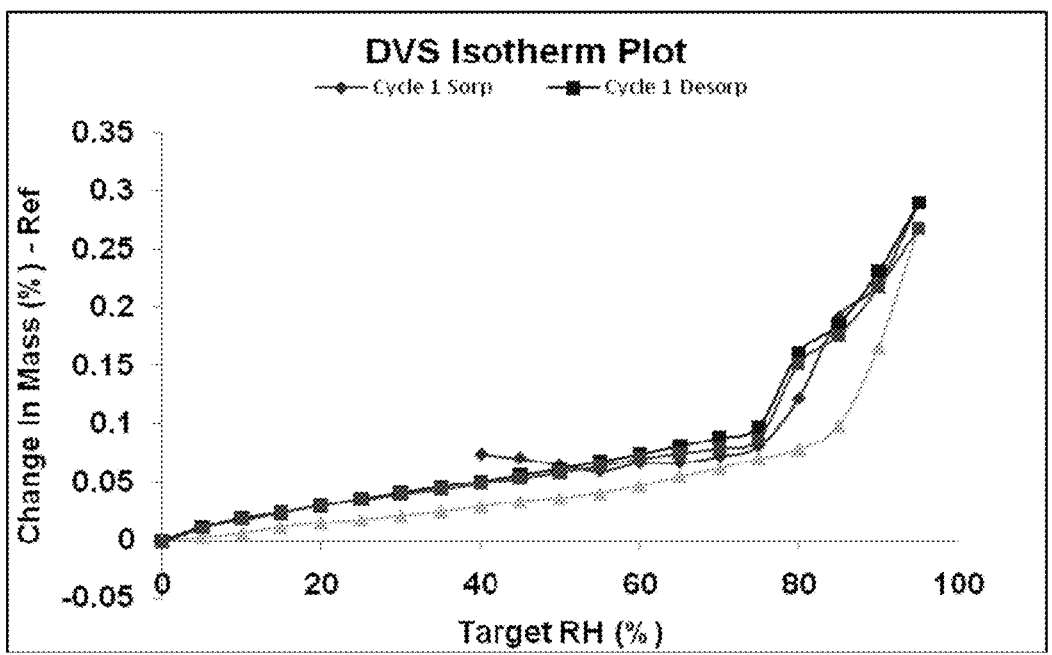
FIG. 12 is a DVS diagram of crystal form A. Experiments show that crystal form A has no or almost no hygroscopicity. In a range of 0-95% RH, the dehydration and hygroscopicity of crystal form A is very weak.
Figure 13:
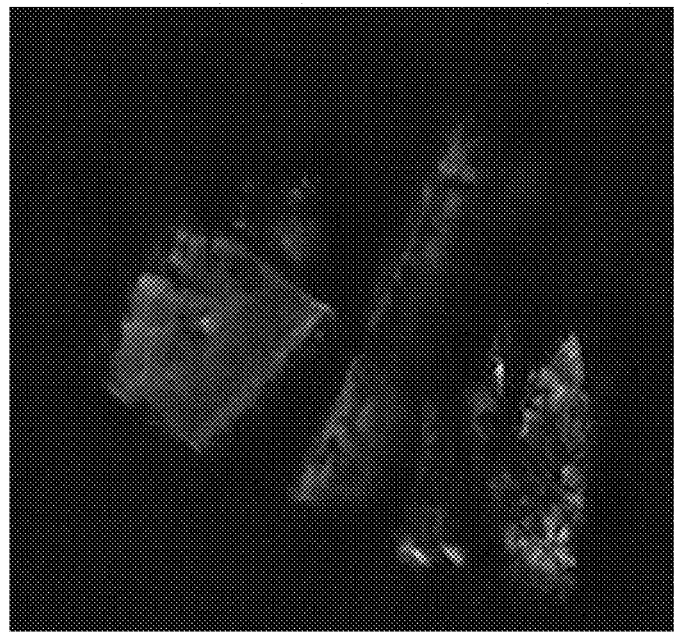
FIG. 13 is a powder polarizing image of crystal form A (200 times).
Figure 14:
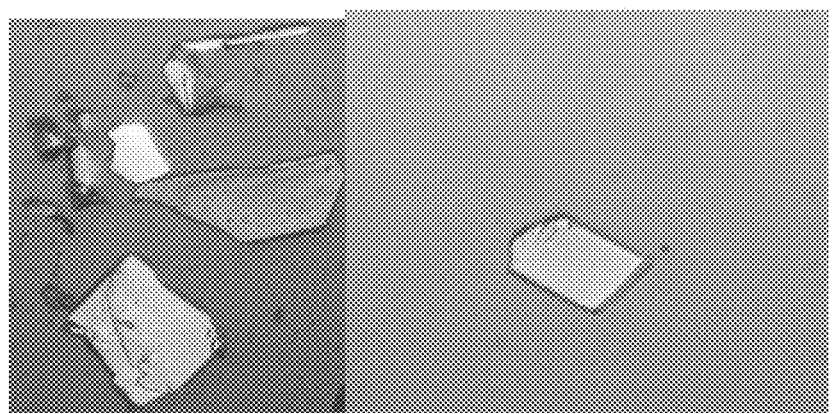
FIG. 14 is a single crystal polarizing image of crystal form A (100 times).
Figure 15:
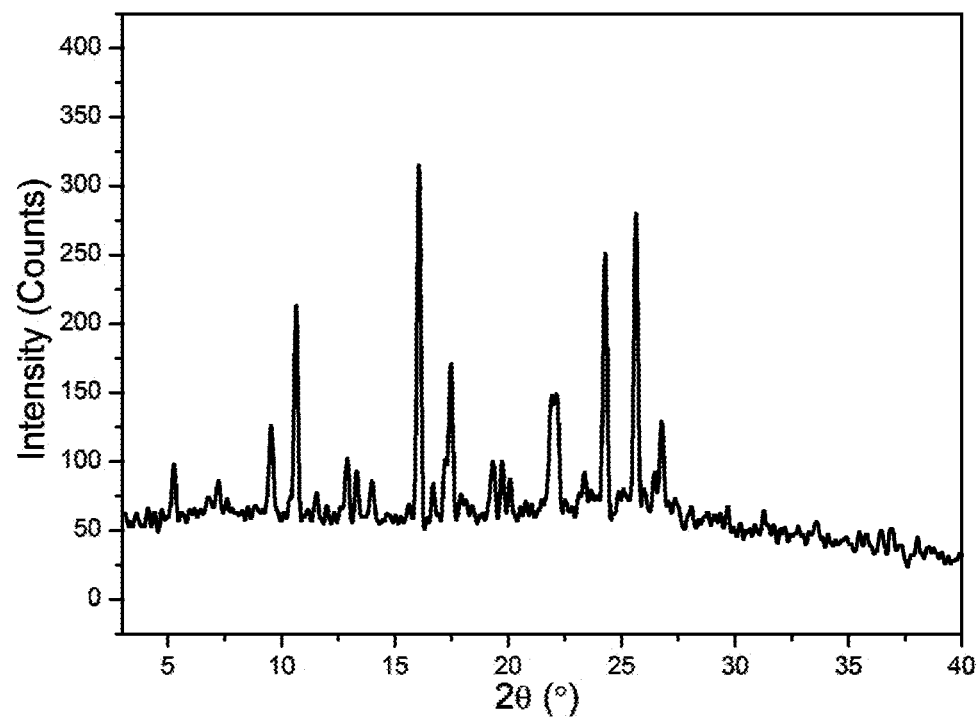
FIG. 15 is an XRPD diagram of crystal form A.

The results of the DVS experiment on the synthetic leonurine sulfate raw material medicine (as shown in FIG. 12) show that the raw material medicine itself is monohydrate crystal form, when the relative humidity is from 0 to 95%, the raw material medicine moisture absorption is about 0.15%, with hygroscopicity. In this invention, it is named as leonurine crystal form A, which is monohydrate crystal form, square block crystal (as shown in FIG. 13), no crystal transformation before melting, dehydrates at 120~150° C. and transform into anhydrous crystal form B, and decomposes at about 250° C. In the range of 0~95% relative humidity, the crystal form does not change, and the hygroscopicity changed slightly, showing no or almost no hygroscopicity. Under the condition of, in the suspension experiment at 25° C., in methanol, ethanol, isopropanol, acetone, acetonitrile, tetrahydrofuran, nitromethane, ethyl acetate, isopropyl acetate, isoamyl alcohol, methyl tert-butyl ether, toluene, methyl isobutyl ketone, n-hexane, n-heptane, ether, dichloromethane, chloroform, petroleum ether, water and other solvents; and under the condition of, in the suspension experiment at 50° C., in methanol, ethanol, acetone, methyl ethyl ketone, isopropyl acetate, methyl tert-butyl ether, toluene, n-hexane, n-heptane, diethyl ether, chloroform, petroleum ether, water and other solvents; and under most solvent conditions in suspension and volatilization of mixed solvents at 25° C. and 50° C., form A can be obtained. FIG. 12 shows the DVS pattern of form A, and the hygroscopicity test results show that Form A has no or almost no hygroscopicity. In a range of 0~95% RH, the dehydration and water absorption behavior of the crystal form is very weak. FIG. 14 shows single crystal polarized photo of crystal form A, single crystal of form A can be obtained by dissolved in acetonitrile/water or methyl ethyl ketone/water or acetone/water=2/1 (V/V) solution, or ethanol/water or acetone/water or methyl ethyl ketone/water or acetonitrile/water or tetrahydrofuran/water=1/1 (V/V) solution, or methyl tert-butyl ether/water/methanol=2/2/1 (V/V/V) solution and then slowly volatilize at room temperature; The separated single crystal of leonurine crystal form A was analyzed by X-ray diffraction, and the data thereof is shown in Table 1, the XRPD diagram is shown in FIG. 15.

The structure of the leonurine crystal form A single crystal was determined by Bruker Smart Apex II single crystal X-ray diffractometer, instrument parameters: light source: Mo target; X-ray: Mo—K (=0.71073 Å); detector: CCD surface detector; resolution: 0.77 Å; current voltage: 50 kV, 30 mA; exposure time: 10 s; surface detector to sample distance: 50 mm; test temperature: 296 (2) K. The structure of leonurine crystal form A single crystal was analyzed by analyzing its X-ray diffraction data.

Structural analysis and refine process: after the integration by substitution of the diffraction data by the SAINT program, the data is subjected to empirical absorption correction using the SADABS program. The single crystal structure was analyzed by direct method using SHEXLT2014, and the structure was refined by least square method; the hydrogen atom refinement process was obtained by isotropic calculation; the hydrogen atoms on O and N are obtained by residual electron density; the hydrogen atoms on C—H are obtained by calculation of hydrogenation, and refine it by adopting the riding model.

Figure 16:
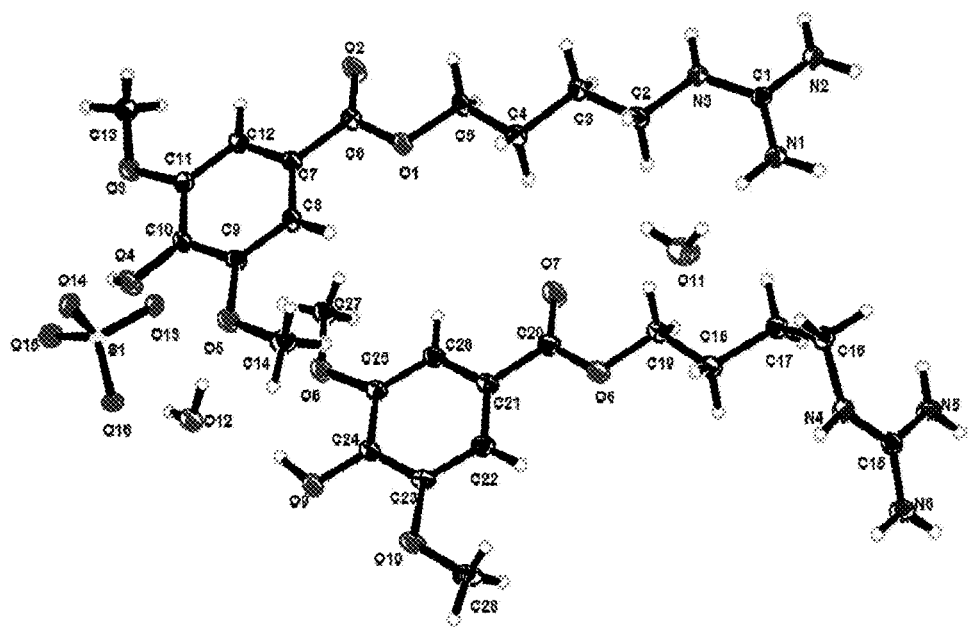
FIG. 16 is the molecular structure of leonurine crystal form A.
Figure 17:
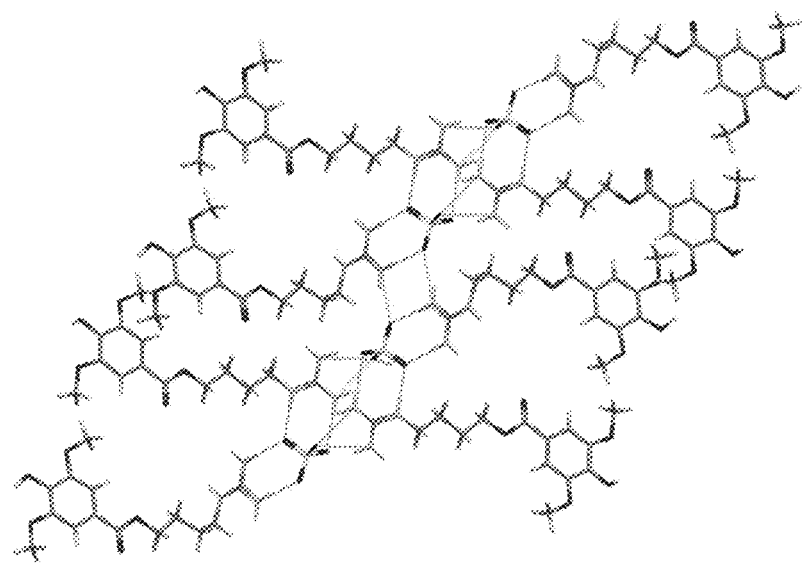
FIG. 17 is the two-dimensional molecular structure of leonurine crystal form A.
Figure 18:
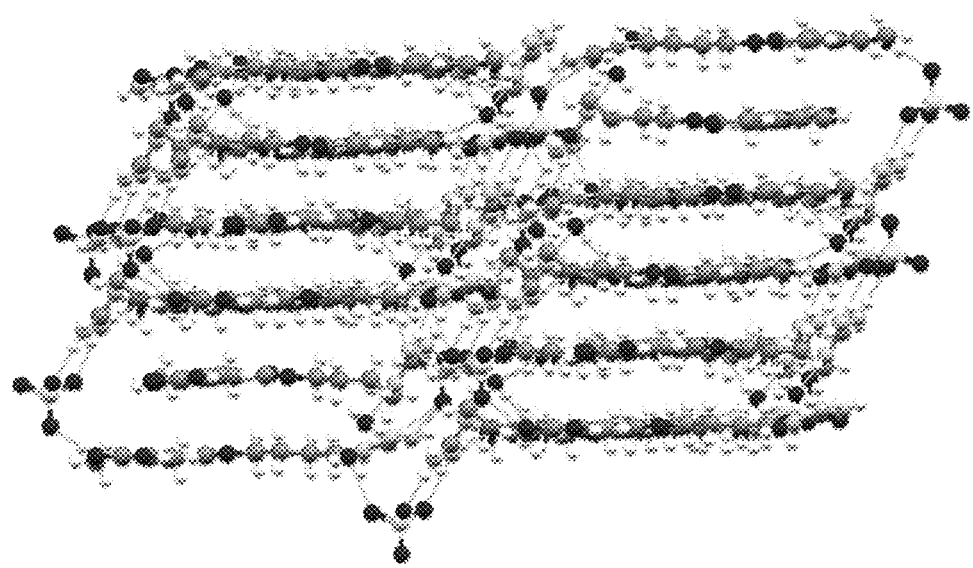
FIG. 18 is the three-dimensional molecular structure of leonurine crystal form A.

The above measurement and data analysis gave the single crystal data of the leonurine crystal form A as shown in Table 9; the spatial positional parameters of all atoms in the molecule are shown in Table 10, based on the above data, the molecular structure of the leonurine crystal form A is depicted (FIG. 16). The leonurine crystal form A is hemisulfate monohydrate, is colorless lamellar crystal (FIG. 14). It belongs to monoclinic system, space group is P-1. The asymmetric unit contains two leonurine molecules, one sulfate ion and two water molecules. The guanidyls in two leonurine molecules and the sulfate ion form an ion bond trimer, a two-dimensional structure is formed between two trimers by hydrogen bondings of the guanidyls and the sulfate ions, to form a multimeric molecular plane layer (FIG. 17). The multi-layered multimeric molecular plane are superimposed in a parallel form, the two-dimensional structure molecular plane forms a three-dimensional laminated network structure of the leonurine crystal form A by hydrogen bondings of water molecules (FIG. 18). Three-dimensional structure shows that the hydrophilic layers formed by guanidyls and sulfate ions and the hydrophobic groups of leonurine are alternately arranged.

TABLE 9

Data of leonurine crystal form A single crystal

| | |
|---|---|
| Molecular Formula | $C_{28}H_{48}N_6O_{16}S$ |
| Crystal form | A |
| Collecting Temperature | 296 K |
| X-ray Generator | Mo Kα |
| Crystal Color | Colorless and transparent |
| Crystal Shape | lamellar |
| Crystal System | triclinic |
| Space Group | P-1 |
| Unit Cell Parameters | a = 7.857(5) Å |
| | b = 13.913(8) Å |
| | c = 17.314(10) Å |
| | α = 103.993(12)° |
| | β = 99.612(12)° |
| | γ = 100.482(15)° |
| Unit Cell Volume | 1761.2(18) Å$^3$ |
| Calculate Density | 1.427 mg/cm$^3$ |

TABLE 10

Spatial positional parameters of all atoms in leonurine single crystal form A (Functional atomic coordinates and isotropic or equivalent isometric displacement parameters)

| | x | y | z | $U_{iso}$*/$U_{eq}$ |
|---|---|---|---|---|
| O1 | 0.2706 (3) | 0.97028 (15) | 0.55640 (12) | 0.0300 (5) |
| O2 | 0.3705 (3) | 1.10861 (17) | 0.51794 (13) | 0.0447 (6) |
| O3 | 0.0092 (3) | 1.01092 (15) | 0.22144 (12) | 0.0338 (5) |
| O4 | −0.1928 (3) | 0.82326 (16) | 0.20137 (12) | 0.0341 (5) |
| H4 | −0.1505 | 0.8377 | 0.1630 | 0.051* |
| O5 | −0.1885 (3) | 0.73474 (15) | 0.31752 (12) | 0.0346 (5) |
| N1 | 0.5878 (3) | 0.85074 (18) | 0.95391 (15) | 0.0323 (6) |
| H1A | 0.4982 | 0.8173 | 0.9127 | 0.039* |
| H1B | 0.6269 | 0.8205 | 0.9901 | 0.039* |
| N2 | 0.7988 (3) | 0.99643 (18) | 1.02438 (14) | 0.0319 (6) |
| H2A | 0.8498 | 1.0603 | 1.0301 | 0.038* |
| H2B | 0.8369 | 0.9655 | 1.0603 | 0.038* |
| N3 | 0.6076 (3) | 0.99373 (18) | 0.90795 (14) | 0.0284 (6) |
| H3 | 0.6512 | 1.0596 | 0.9188 | 0.034* |
| C1 | 0.6638 (4) | 0.9466 (2) | 0.96149 (17) | 0.0243 (6) |
| C2 | 0.4778 (4) | 0.9423 (2) | 0.83226 (17) | 0.0289 (7) |
| H2C | 0.3569 | 0.9326 | 0.8431 | 0.035* |
| H2D | 0.4989 | 0.8745 | 0.8086 | 0.035* |
| C3 | 0.4922 (4) | 1.0054 (2) | 0.77270 (17) | 0.0293 (7) |
| H3A | 0.6173 | 1.0225 | 0.7680 | 0.035* |
| H3B | 0.4577 | 1.0700 | 0.7942 | 0.035* |
| C4 | 0.3752 (4) | 0.9502 (2) | 0.68841 (17) | 0.0290 (7) |

TABLE 10-continued

Spatial positional parameters of all atoms in leonurine single crystal form A (Functional atomic coordinates and isotropic or equivalent isometric displacement parameters)

| | x | y | z | $U_{iso}*/U_{eq}$ |
|---|---|---|---|---|
| H4A | 0.4108 | 0.8863 | 0.6657 | 0.035* |
| H4B | 0.2498 | 0.9324 | 0.6925 | 0.035* |
| C5 | 0.3941 (4) | 1.0176 (2) | 0.63333 (16) | 0.0280 (7) |
| H5A | 0.3707 | 1.0843 | 0.6589 | 0.034* |
| H5B | 0.5167 | 1.0295 | 0.6247 | 0.034* |
| C6 | 0.2735 (4) | 1.0259 (2) | 0.50316 (17) | 0.0277 (6) |
| C7 | 0.1451 (4) | 0.9732 (2) | 0.42395 (17) | 0.0262 (6) |
| C8 | 0.0364 (4) | 0.8775 (2) | 0.41243 (17) | 0.0262 (6) |
| H8 | 0.0396 | 0.8461 | 0.4555 | 0.031* |
| C9 | −0.0761 (4) | 0.8290 (2) | 0.33707 (17) | 0.0260 (6) |
| C10 | −0.0784 (4) | 0.8749 (2) | 0.27377 (16) | 0.0252 (6) |
| C11 | 0.0285 (4) | 0.9717 (2) | 0.28693 (17) | 0.0265 (6) |
| C12 | 0.1422 (4) | 1.0215 (2) | 0.36255 (16) | 0.0253 (6) |
| H12 | 0.2163 | 1.0871 | 0.3719 | 0.030* |
| C13 | 0.0999 (5) | 1.1133 (2) | 0.23333 (19) | 0.0384 (8) |
| H13A | 0.0766 | 1.1313 | 0.1819 | 0.058* |
| H13B | 0.2277 | 1.1205 | 0.2515 | 0.058* |
| H13C | 0.0579 | 1.1588 | 0.2748 | 0.058* |
| C14 | −0.1957 (5) | 0.6871 (2) | 0.3817 (2) | 0.0407 (8) |
| H14A | −0.2797 | 0.6205 | 0.3607 | 0.061* |
| H14B | −0.2347 | 0.7300 | 0.4259 | 0.061* |
| H14C | −0.0775 | 0.6780 | 0.4026 | 0.061* |
| O6 | 0.5617 (3) | 0.41591 (16) | 0.38037 (12) | 0.0338 (5) |
| O7 | 0.4343 (3) | 0.28020 (18) | 0.41548 (14) | 0.0529 (7) |
| O8 | 0.7916 (3) | 0.34316 (17) | 0.70748 (13) | 0.0415 (6) |
| O9 | 1.0084 (3) | 0.52479 (17) | 0.74073 (13) | 0.0388 (6) |
| O10 | 1.0101 (3) | 0.63530 (16) | 0.63798 (13) | 0.0425 (6) |
| N4 | 0.5054 (3) | 0.53333 (18) | 0.10860 (14) | 0.0296 (6) |
| H4C | 0.6177 | 0.5643 | 0.1294 | 0.036* |
| N5 | 0.2264 (3) | 0.54760 (18) | 0.05537 (15) | 0.0344 (6) |
| H5C | 0.1882 | 0.4810 | 0.0419 | 0.041* |
| H5D | 0.1529 | 0.5857 | 0.0445 | 0.041* |
| N6 | 0.4516 (3) | 0.69053 (18) | 0.11043 (16) | 0.0352 (6) |
| H6A | 0.3785 | 0.7284 | 0.0983 | 0.042* |
| H6B | 0.5632 | 0.7192 | 0.1348 | 0.042* |
| C15 | 0.3934 (4) | 0.5902 (2) | 0.09185 (17) | 0.0273 (6) |
| C16 | 0.4560 (4) | 0.4229 (2) | 0.09497 (18) | 0.0305 (7) |
| H16A | 0.5634 | 0.3956 | 0.0923 | 0.037* |
| H16B | 0.3715 | 0.3919 | 0.0416 | 0.037* |
| C17 | 0.3724 (4) | 0.3918 (2) | 0.16078 (18) | 0.0332 (7) |
| H17A | 0.3434 | 0.3166 | 0.1479 | 0.040* |
| H17B | 0.2600 | 0.4144 | 0.1606 | 0.040* |
| C18 | 0.4931 (4) | 0.4366 (2) | 0.24612 (17) | 0.0314 (7) |
| H18A | 0.6187 | 0.4432 | 0.2421 | 0.038* |
| H18B | 0.4765 | 0.5054 | 0.2706 | 0.038* |
| C19 | 0.4504 (4) | 0.3691 (2) | 0.29975 (17) | 0.0345 (7) |
| H19A | 0.3238 | 0.3603 | 0.3024 | 0.041* |
| H19B | 0.4722 | 0.3011 | 0.2769 | 0.041* |
| C20 | 0.5404 (4) | 0.3608 (2) | 0.43333 (18) | 0.0323 (7) |
| C21 | 0.6630 (4) | 0.4073 (2) | 0.51512 (17) | 0.0283 (7) |
| C22 | 0.7778 (4) | 0.5035 (2) | 0.53459 (18) | 0.0316 (7) |
| H22 | 0.7771 | 0.5420 | 0.4961 | 0.038* |
| C23 | 0.8931 (4) | 0.5422 (2) | 0.61116 (18) | 0.0310 (7) |
| C24 | 0.8936 (4) | 0.4849 (2) | 0.66691 (17) | 0.0287 (7) |
| C25 | 0.7767 (4) | 0.3908 (2) | 0.64644 (18) | 0.0287 (7) |
| C26 | 0.6610 (4) | 0.3505 (2) | 0.57091 (18) | 0.0297 (7) |
| H26 | 0.5821 | 0.2855 | 0.5575 | 0.036* |
| C27 | 0.6701 (4) | 0.2497 (2) | 0.69559 (19) | 0.0374 (8) |
| H27A | 0.7000 | 0.2226 | 0.7420 | 0.056* |
| H27B | 0.6765 | 0.2011 | 0.6453 | 0.056* |
| H27C | 0.5496 | 0.2608 | 0.6912 | 0.056* |
| C28 | 1.0149 (5) | 0.6960 (2) | 0.5826 (2) | 0.0446 (9) |
| H28A | 1.1095 | 0.7580 | 0.6069 | 0.067* |
| H28B | 0.9006 | 0.7145 | 0.5713 | 0.067* |
| H28C | 1.0378 | 0.6573 | 0.5316 | 0.067* |
| S1 | 0.01981 (10) | 0.76948 (5) | 0.03277 (4) | 0.0261 (2) |
| O13 | 0.1906 (3) | 0.81191 (16) | 0.09135 (14) | 0.0414 (6) |
| O14 | −0.1179 (3) | 0.81781 (16) | 0.06340 (12) | 0.0334 (5) |
| O15 | 0.0315 (3) | 0.78906 (16) | −0.04547 (13) | 0.0369 (5) |
| O16 | −0.0327 (3) | 0.65947 (15) | 0.02365 (13) | 0.0342 (5) |
| O11 | 0.7557 (3) | 0.27715 (18) | 0.15072 (15) | 0.0474 (6) |
| H11A | 0.7592 | 0.2361 | 0.1799 | 0.071* |
| H11B | 0.7949 | 0.2554 | 0.1085 | 0.071* |
| O12 | 0.8776 (3) | 0.60262 (16) | 0.16410 (13) | 0.0380 (5) |

TABLE 10-continued

Spatial positional parameters of all atoms in leonurine single crystal form A (Functional atomic coordinates and isotropic or equivalent isometric displacement parameters)

|  | x | y | z | $U_{iso}*/U_{eq}$ |
|---|---|---|---|---|
| H12A | 0.9110 | 0.6250 | 0.1262 | 0.057* |
| H12B | 0.8846 | 0.6524 | 0.2051 | 0.057* |
| H9 | 1.012 (5) | 0.474 (2) | 0.767 (2) | 0.054 (11)* |

EXAMPLE 5

Accelerated Stability Tests of Various Leonurine Crystal Forms and Selection of Dominant Crystal Form After being placed in a stability chamber at 40° C. and 70% relative humidity for 10 days, the crystal forms A and E remain unchanged, and the crystal form B, crystal form C, crystal form D, and form F are all transformed into crystal form A;

At 40° C. and relative humidity of 60%-80%, the 10-day stability test (Table 11) showed that the leonurine crystal form A was most stable, with no crystal transformation behavior, and the hygroscopicity was not obvious. The crystal form B, C, D and F all appeared crystal transformation; although the crystal form E did not appear crystal transformation, the hygroscopicity is strong, and the hygroscopicity is about ten times that of the crystal form A. Therefore, leonurine crystal form A is the preferred medicinal crystal form, it is a monohydrate with stable performance and can be obtained repeatedly by various conditions.

TABLE 11

Comparison of various new leonurine crystal forms

| Crystal Form | Melting point | hygroscopicity | Crystal stability |
|---|---|---|---|
| A | — | 60% RH, water absorption 0.07% 80% RH, water absorption 0.12% | stable |
| B | 190.8° C. | 60% RH, water absorption 0.14% 80% RH, water absorption 0.30% | 40° C., 70% RH, 10 days, transform into A |
| C | — | 60% RH, water absorption 0.56% 80% RH, water absorption 1.05% | 40° C., 70% RH, 10 days, transform into A |
| D | — | 60% RH, water absorption 1.63% 80% RH, water absorption 0.98% | 40° C., 70% RH, 10 days, transform into A |
| E | — | 60% RH, water absorption 0.07% 80% RH, water absorption 0.12% | stable |
| F | 192.2° C. | 60% RH, water absorption 0.14% 80% RH, water absorption 0.30% | 40° C., 70% RH, 10 days, transform into A |

Where: RH: Relative Humidity

EXAMPLE 6

Figure 19:
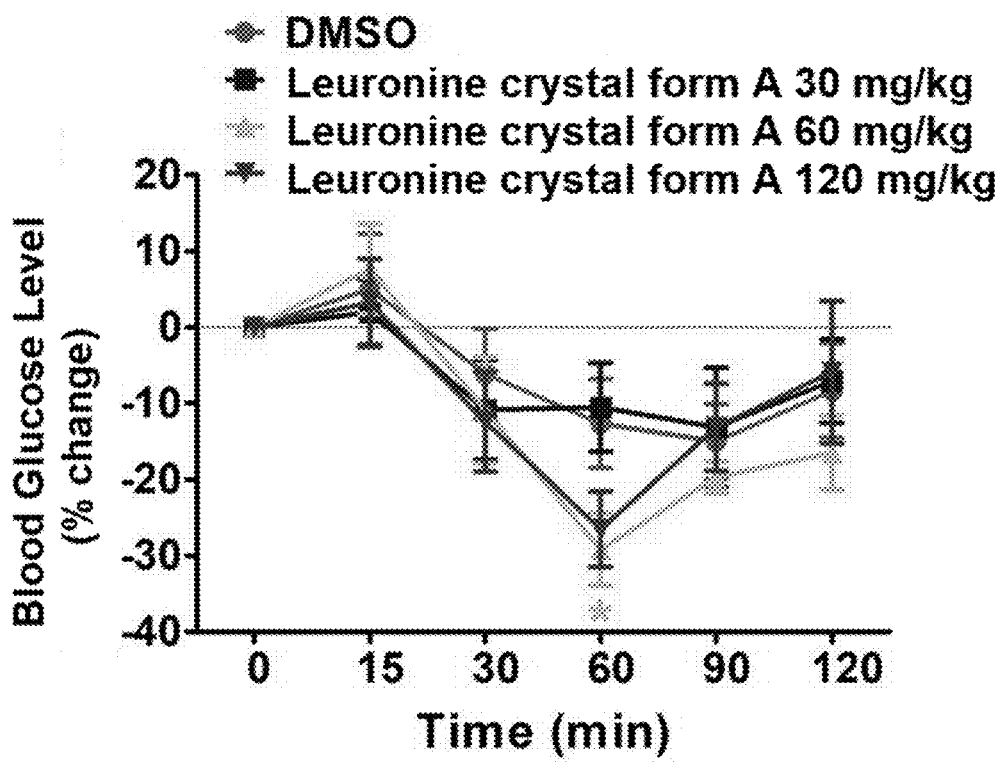
FIG. 19 shows the effects of three kinds of dosage of one acute administration of leonurine crystal form A on insulin sensitivity curve, where the insulin sensitivity curve of the 60 mg/kg dose group of leonurine crystal form A decreased significantly at the 60 minute time point (P=0.038), indicating that leonurine crystal form A increased the insulin sensitivity of the rat.

Experiment of Single Dosage Acute Administration of Leonurine Crystal Form A to Improve Insulin Sensitivity in Rats Thirty-two Sprague-Dawley male rats (body weight 180-220 g) were randomly divided into 4 groups, gave control solvent and three different doses of leonurine crystal form A respectively. The control solvent group was given an equal volume of DMSO, and the treatment groups were administered with three doses of 30 mg/kg, 60 mg/kg and 120 mg/kg respectively, 8 rats per group, where the leonurine crystal form A was dissolved in DMSO at concentrations of 30 mg/ml, 60 mg/ml and 120 mg/ml respectively. The volume of solvent obtained per rat is one millilitre per kilogram of body weight. The route of administration is gavage, weighing before gavage, and taking blood from tail vein to measure blood glucose. Each rat was tested for insulin sensitivity 1 hour after administration of drugs or control solvent, the dose of insulin selected was 0.5 units per kilogram of body weight, intraperitoneal injection of insulin, blood glucose was measured before injection and at 15, 30, 60, 90, and 120 minutes after injection. The data were analyzed by SPSS 11.5 statistical software, and the results were expressed as mean ±standard error of the mean (mean±SEM), pairwise comparison between groups was examined by one-way analysis of variance (ANOVA), P<0.05 was considered significant difference between the groups. The experiment results (FIG. 19) showed that the downward shift of the insulin sensitivity curve of the rat was observed when leonurine crystal form A was administered at a dose of 60 mg/kg, and downward shift of the curve reached statistical significance (P=0.038) at the 60 minutes time point, indicating that the leonurine crystal form A increased the sensitivity of the rat to insulin. Compared with the DMSO control group, the leonurine crystal form A had a tendency to move down the insulin sensitivity curve at the 60-minute time point with the dose of 120 mg/kg, but no statistically significant difference was observed (P=0.079). In the 30 mg/kg dose group of leonurine crystal form A, the insulin sensitivity curve was basically coincident with the control group, and there was no statistically significant difference.

EXAMPLE 7

Figure 20:
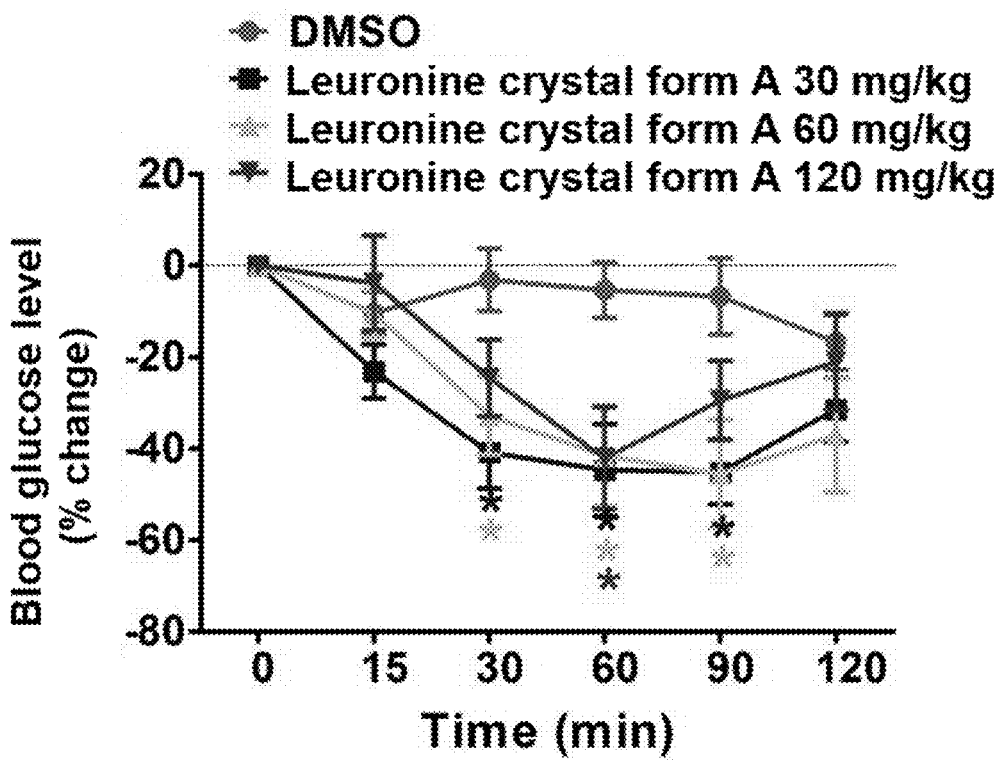
FIG. 20 shows the effects of three kinds of dosage for continuous administration of leonurine crystal form A for 7 days on insulin sensitivity curve, where the insulin sensitivity curves of the 30 and 60 mg/kg/d dose group of leonurine crystal form A decreased significantly at the 30 minute time point (compared with the control group, P=0.004 and P=0.018, respectively); the insulin sensitivity curves of the three dose groups, including 30, 60 and 120 mg/kg/d of leonurine crystal form A, decreased significantly at the 60-minute time point (compared with the control group, P=0.011, P=0.018, and P=0.017); the insulin sensitivity curves of the 30 and 60 mg/kg/d dose group of leonurine crystal form A decreased significantly at the 90-minute time point (compared with the control group, P=0.009 and P=0.008, respectively).

Experiment of Chronic Continuous Administration of Leonurine Crystal Form A to Improve Insulin Sensitivity in Rats Twenty Sprague-Dawley male rats (body weight 180-220 g) were randomly divided into 4 groups, give control solvent and three different doses of leonurine crystal form A respectively. The control solvent group was given an equal volume of DMSO, and the treatment groups were administered at three doses of 30 mg/kg, 60 mg/kg and 120 mg/kg respectively, 5 rats per group, where the leonurine crystal form A was dissolved in DMSO at concentrations of 30 mg/ml, 60 mg/ml and 120 mg/ml respectively. The volume of solvent used per rat is one millilitre per kilogram of body weight. The rats were administered intragastrically with the drugs or control solvent once a day for 7 consecutive days, and performing insulin sensitivity test on the 7th day. The rats were treated with the drugs or control solvent on the day of the test, and weighed before administration, then taking blood from tail vein to measure blood glucose. Each rat was tested for insulin sensitivity 1 hour after administration of the drugs or control solvent, and the rats were not fed food for 4 hours before the insulin sensitivity test to make them fasted but still given water. The insulin dose in the insulin sensitivity test is 0.75 units per kilogram of body weight, and insulin was injected through intraperitonealion. Blood glucose was measured before injection and at 15, 30, 60, 90, and 120 minutes after injection. The data were analyzed by SPSS statistical software (version 11.5), and the results were expressed as mean ±standard error of the mean (mean±SEM). Multiple group comparisons were tested by one-way analysis of variance (ANOVA). P<0.05 was considered as statistically significant. The experiment results (FIG. 20) showed that the downward shift of the insulin sensitivity curve of the rat was observed when leonurine crystal form A was administered at a dose of 30, 60 and 120 mg/kg/d. The insulin sensitivity curve was moved down significantly by different doses of the leonurine crystal form A at three time points (30 min, 60 min and 90 min). At 30 minutes point, leonurine crystal form A increased insulin sensitivity in both 30 and 60 mg/kg/d dose groups (P=0.004 and P=0.018, respectively) compared with the control group. At 60 minutes point, leonurine crystal form A increased insulin sensitivity in both 30, 60 and 120 mg/kg/d dose groups (P=0.011, P=0.018 and P=0.017) compared with the control group. At 90 minutes point, leonurine crystal form A increased insulin sensitivity in both 30 and 60 mg/kg/d dose groups(P=0.009 and P=0.008, respectively) compared with the control group. The above experiment results show that chronic continuous administration of leonurine crystal form A can increase insulin sensitivity.

EXAMPLE 8

Experiment of Chronic Continuous Administration of Leonurine Crystal Form A Reduced Body Weight, Fasting Blood Glucose and Increased Glucose Tolerance in Rats Forty male Sprague-Dawley rats weighed 180 to 220 g were randomly divided into 4 groups (10 rats each group): control group are treated with equal volume of DMSO, and the treatment groups were administered at 30 mg/kg per day, 60 mg/kg per day, and 120 mg/kg per day of leonurine crystal form A respectively, where leonurine crystal form A was dissolved in DMSO at concentrates of 30 mg/ml, 60 mg/ml and 120 mg/ml, and the volume of vehicle administered intragastrically in each rat was 1 ml per kg of body weight. The rats were treated with leonurine crystal form A or DMSO once a day continuously for 3 weeks, and the body weight and fasting blood-glucose were detected at third week. The rats were fasted (allowed water ad libitum) for 12 h before experiment. Fasting blood-glucose and body weight were tested after 1 h of administered drugs. The rats were not given drugs on the next days for one week, and the body weight and fasting blood-glucose were detected at forth week. The data were analyzed by SPSS statistical software (version 11.5), and results were expressed as the mean±standard error of the mean (mean±SEM). Multiple group comparisons were tested by one-way analysis of variance (ANOVA). P<0.05 was considered as statistically significant.

Figure 21:
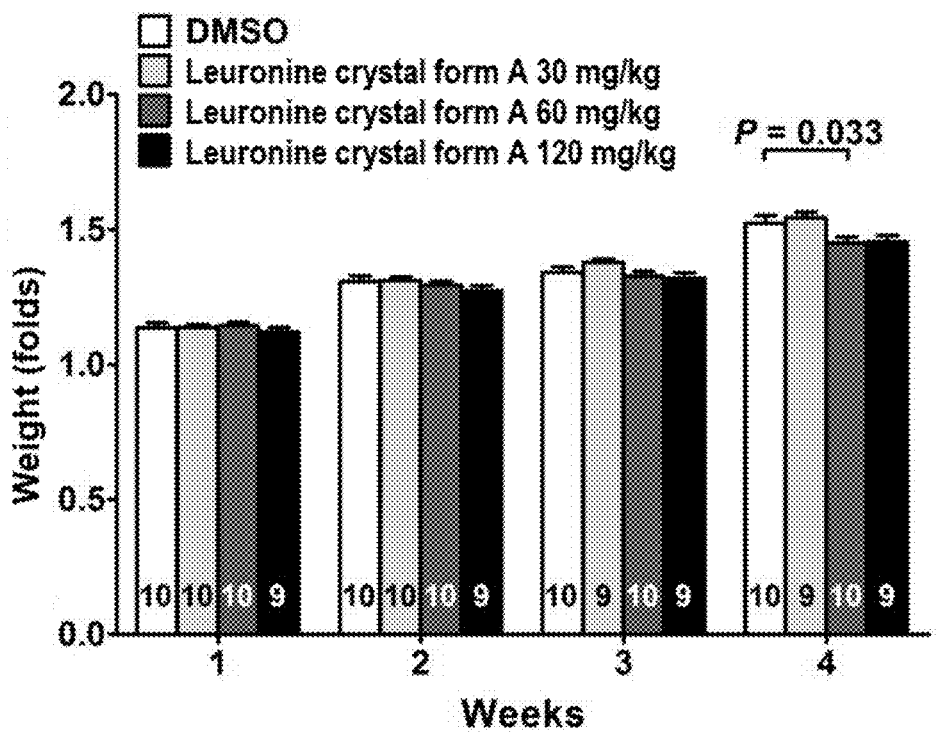
FIG. 21 shows the effects of chronic administration of leonurine crystal form A for 3 weeks on weight of rats. At the fourth week (one week after discontinuation), it was observed that leonurine crystal form A significantly decreased the weight of rats when the group dose was 60 mg/kg/d (compared with the solvent control group, P=0.033); however, the 120 mg/kg/d dose group of leonurine crystal form A had a declining trend of weight, but the difference was not statistically significant (compared with the solvent control group, P=0.057).

The results suggested that the body weight of rats was significantly reduced at fourth week (the drug discontinued for one week) after administration of leonurine crystal form A at the dose of 60 mg/kg/d continuously for 3 weeks (p=0.033 vs vehicle group). The body weight of rats administrated of leonurine crystal form A at the dose of 120 mg/kg/d had the trend to reduce, but had not statistically difference (p=0.057 vs vehicle group) (FIG. 21).

Figure 22:
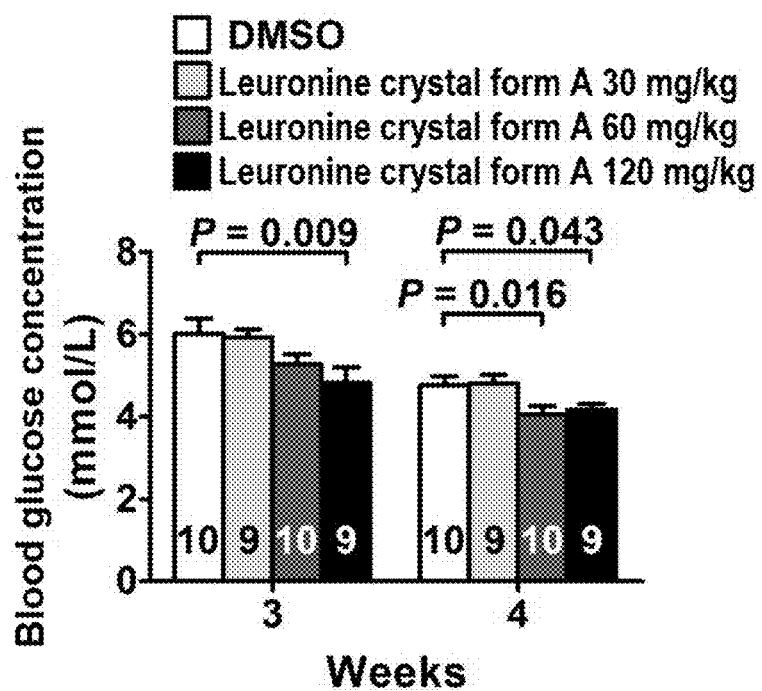
FIG. 22 shows the effects of chronic administration of leonurine crystal form A for 3 weeks on fasting blood glucose of rats. After 3 weeks of continuous administration, the 120 mg/kg/d dose group of leonurine crystal form A significantly decreased fasting blood glucose of rats (compared with the solvent control group, P=0.009); however, the 60 mg/kg/d dose group of leonurine crystal form A had a declining trend of fasting blood glucose, but the difference was not statistically significant (compared with the solvent control group, P=0.083). At the fourth week, it was observed that both the 60 and 120 mg/kg/d dose groups of leonurine crystal form A decreased fasting blood glucose (compared with the solvent control group, P=0.016 and 0.043, respectively).

Fasting blood-glucose results showed significant reduce after administration of leonurine crystal form A at the dose of 120 mg/kg/d (p=0.009 vs vehicle group), but had not statistically difference at the dose of 60 mg/kg/d (p=0.083 vs vehicle group), after continuously administrated for 3 weeks (FIG. 22). However, fasting blood-glucose of rats were both significantly reduced after administration of leonurine crystal form A at the dose of 60 mg/kg/d and 120 mg/kg/d at forth week (p=0.016 and p=0.043 vs vehicle group, respectively) (FIG. 22).

Eighteen male Sprague-Dawley rats weighed 180 to 220 g were randomly divided into 4 groups, and with vehicle or three different dose of leonurine crystal form A treatment respectively: control group are treated with equal volume of DMSO, and treatment groups are treated with 30 mg/kg per day, 60 mg/kg per day, or 120 mg/kg per day of leonurine crystal form A. Leonurine crystal form A was dissolved in DMSO at concentrates of 30 mg/ml, 60 mg/ml and 120 mg/ml, and the volume of vehicle administered intragastrically in each rat was 1 ml per kg of body weight. The rats were treated with leonurine crystal form A or DMSO once a day for 3 weeks. Oral glucose tolerance test (OGTT) was detected at third week, and the rats were fasted 12 h before OGTT experiment. OGTT experiment was performed 1 h after administered of drugs. Blood glucose and body weight were tested before OGTT. OGTT: Rats were given 25% glucose solution (2 g/kg of body weight, 8 ml/kg) by intraperitoneal injection, and blood glucose concentration was determined from the tail vein at 15, 30, 60 and 120 min. The drug was discontinued for one week after OGTT, and the body weight and fasting blood-glucose were detected at forth week.

Figure 23:
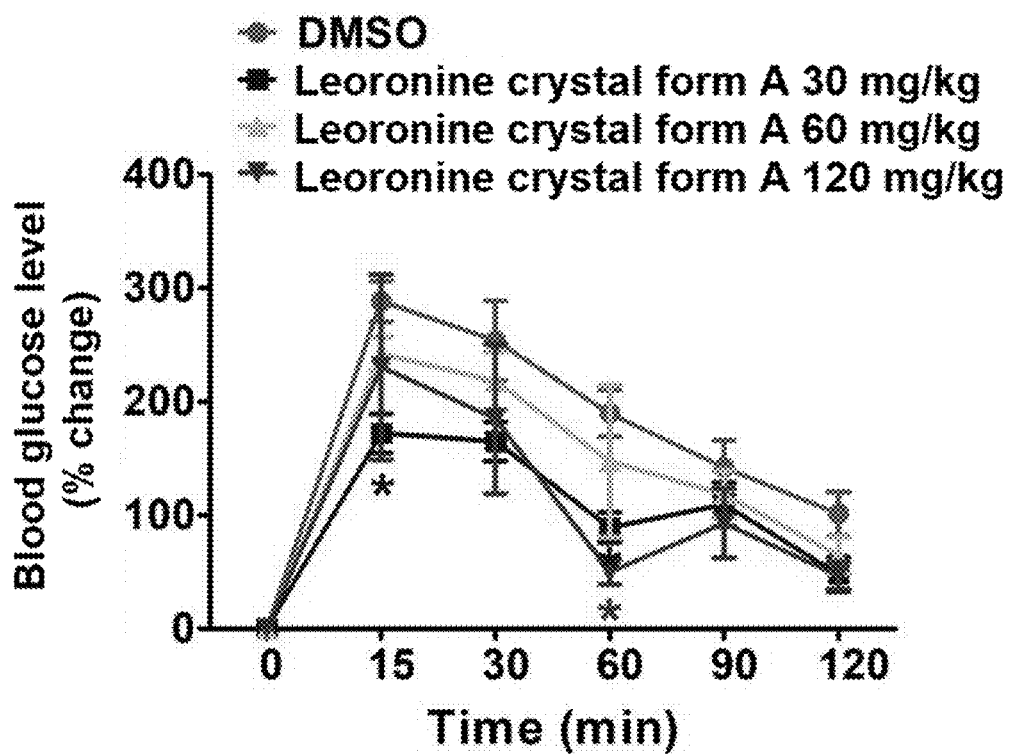
FIG. 23 shows the effects of chronic administration of leonurine crystal form A for 3 weeks on glucose tolerance tests of rats, leonurine crystal form A could significantly decreased the glucose tolerance curve at the 15- and 60 minute-time point; at the 15 minutes time point, the glucose tolerance curve moved down, and the 30 mg/kg/d dose group of leonurine crystal form A could decrease the level of blood glucose, improve the body's tolerance to glucose when (compared with the solvent control group, P=0.012); at the 60-minute time point, the glucose tolerance curve also moved down, and the 30 and 120 mg/kg/d dose groups of leonurine crystal form A could decrease the level of blood glucose, improve the body's tolerance to glucose (compared with the solvent control group, P=0.026 and 0.005, respectively).
Figure 24:
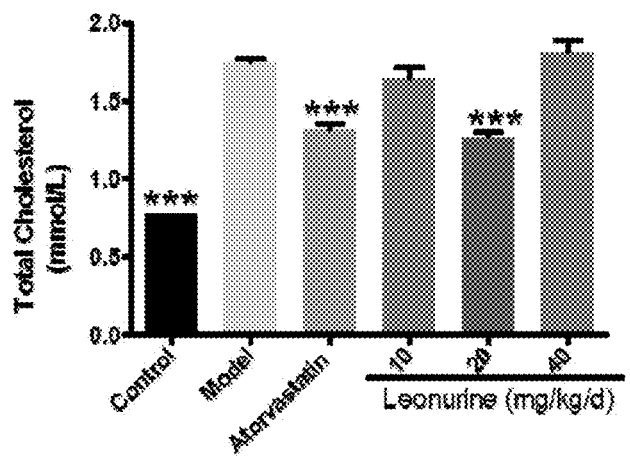
FIG. 24 shows that chronic continuous administration of leonurine crystal form A could decrease the level of serum total cholesterol (TC) of hyperlipidemia mice. Total cholesterol (TC); Control; Model; Leonurine; ***, compared to the model group, P<0.001.

The data were analyzed by SPSS statistical software (version 11.5), and results were expressed as the mean±standard error of the mean (mean±SEM). Multiple group comparisons were tested by one-way analysis of variance (ANOVA). P<0.05 was considered as statistically significant. The glucose tolerance test showed that the glucose tolerance curve was significantly decreased at both 15 and 60 min time points. At 15 min time point, the glucose tolerance curve was shifted down. And the leonurine crystal form A at the dose of 30 mg/kg/d could reduce the degree of elevation of blood glucose and increase the tolerance of glucose to the body (P=0.012 vs vehicle group) (FIG. 23). Moreover, at 60 min time point, the glucose tolerance curve also was moved down at the dose of 30 mg/kg/d and 120 mg/kg/d. The leonurine crystal form A at the dose of 30 mg/kg/d and 120 mg/kg/d could both reduce the degree of elevation of blood glucose and increase the tolerance of glucose to the body (P=0.026 and P=0.005 vs vehicle group, respectively) (FIG. 23).

The results suggested leonurine crystal form A can reduce body weight, fasting blood glucose and increase glucose tolerance in rats. Based on the previous toxicological study showed that the toxicity of leonurine crystal form A was very low, and far lower than the toxic dose. Therefore, the leonurine crystal form A can be considered with the therapeutic effect of disease instead of toxic effects.

EXAMPLE 9

Experiment of Chronic Continuous Administration of Leonurine Crystal Form A Reduced Lipid in Hyperlipidemia Mice Fifteen C57BL/6J mice (male, 6-8 weeks) and seventy-five ApoE knockout mice (male, 6-8 weeks) were used for experiments. C57BL/6J mice were fed with normal diet, and ApoE knockout mice were fed for 1 week with a diet of normal/high fat diet ratio of 1/1. All the mice were randomly divided into 6 groups (C57BL/6J mice as a group):
1) Control group (C57B/6J, Normal diet, n=15); Administered intragastrically with ultrapure water;
2) Model group (Vehicle group, ApoE, High fat diet, n=15); Administered intragastrically with ultrapure water;
3) Leonurine crystal form A in low dose group (ApoE, High fat diet, n=15); Administered intragastrically at a dose of 10 mg/kg/day;
4) Leonurine crystal form A in middle dose group (ApoE, High fat diet, n=15); Administered intragastrically at a dose of 20 mg/kg/day;
5) Leonurine crystal form A in high dose group (ApoE, High fat diet, n=15); Administered intragastrically at a dose of 40 mg/kg/day;
6) Atorvastatin group (Positive control group, ApoE, High fat diet, n=15); Administered intragastrically at a dose of 3 mg/kg/day;

Mice were weighed before administered drugs every week, where the dosage of the drug for mice is calculate according to the weight; and housed under 24±1° C. room temperature and 55±5% air humidity condition, and allowed enough food and water ad libitum. After the drug administration continuously for 4 weeks, the mice were anesthetized with pentobarbital sodium according to body weight. Blood (0.5 ml per mouse) was drawn from the inner canthus vein for hematology analysis. Hematology analysis: blood samples were let for standing for 2 h and centrifuged (3000 rpm, 10 min, 4° C.) to obtain serum. The total cholesterol (TC), triacylglycerol (TG) and low-density cholesterol (LDL-C) levels in the serum samples were assessed using automatic biochemical analyzer. Statistical analysis: GraphPad Prism 5 software was used to analyze and draw figure. Results were expressed as the mean±standard (mean±SD), and statistical analysis was performed by one-way analysis of variance (ANOVA) or student's t test. A difference with $P<0.05$ was considered statistically significant. Statistical significance was set at *$P<0.05$, $P<0.01$, *$P<0.001$ versus the model group. The results suggested that the total cholesterol in the serum of ApoE knockout mice fed with high fat diet was higher than wide type fed with normal diet. Atorvastatin group and leonurine crystal form A in middle dose group reduced the total cholesterol in the serum compared with model group (vehicle group).

Figure 25:
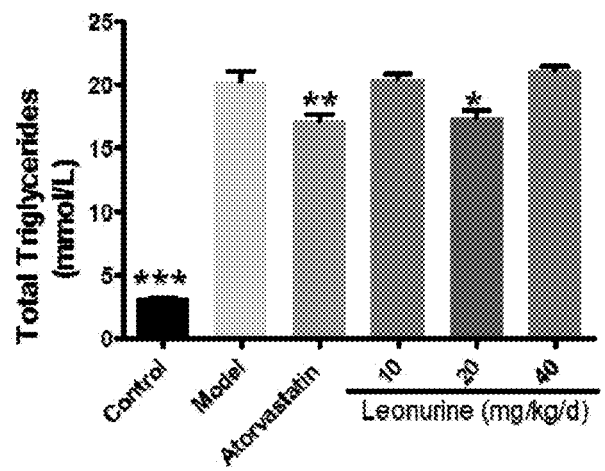
FIG. 25 shows that leonurine crystal form A (medium dose group) could decrease the level of serum triglyceride of ApoE knockout mice. Total triacylglycerol (TG); Control; Model; Leonurine; *, compared to the model group, P<0.05; , compared to the model group, P<0.01; *, compared to the model group, P<0.001.

The results suggested that the triacylglycerol in the serum of ApoE knockout mice fed with high fat diet was higher than wide type (C57BL/J) fed with normal diet. Atorvastatin group and leonurine crystal form A in middle dose group both reduced the triacylglycerol in the serum compared with model group (vehicle group) (FIG. 25).

Figure 26:
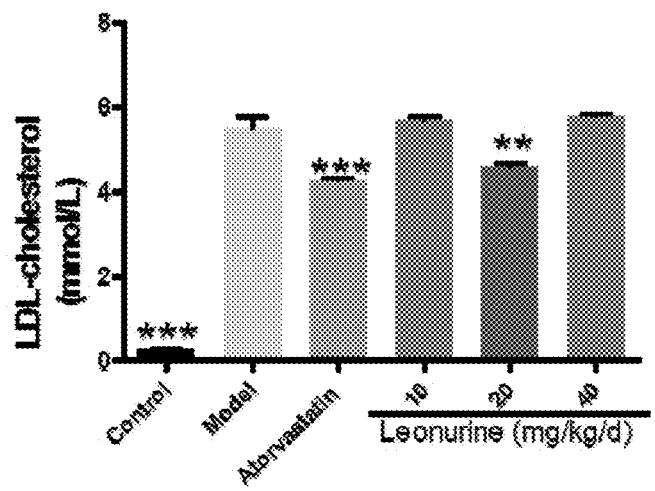
FIG. 26 shows that leonurine crystal form A (medium dose group) could decrease the level of serum low density lipoprotein of ApoE knockout mice. LDL-cholesterol (LDL); Control; Model; Leonurine; , compared to the model group, P<0.01; *, compared to the model group, P<0.001.

The results showed that the low-density cholesterol (LDL-C) levels in the serum of ApoE knockout mice fed with high fat diet was higher than wide type (C57BL/J) fed with normal diet. Atorvastatin group and leonurine crystal form A in middle dose group both reduced the LDL-C levels in the serum compared with model group (FIG. 26).

The results suggested that chronic continuous administration of leonurine crystal form A for 4 weeks could reduce the total cholesterol, triacylglycerol and low-density cholesterol levels in the serum of ApoE knockout hyperlipidemia mice. Given that the total cholesterol, triacylglycerol and low-density cholesterol are independent risk factors for cardiovascular diseases, such as atherosclerosis, the effects of leonurine crystal form A can be used to treat disorders of lipid metabolism diseases characterized in high cholesterol, triglycerides and low-density lipids, which in turn reduces the risk of cardiovascular diseases, such as secondary atherosclerosis.

EXAMPLE 10

Experiment of Chronic Continuous Administration of Leonurine Crystal Form A Reduced Total Cholesterol and Triacylglycerol in Hyperlipidemia Rabbits Forty-eight male New Zealand rabbits weighed 1.8 to 2.2 kg were housed under 12 h dark-12 h light cycles and allowed food and water ad libitum to adapt to the housing environment for one week, and then randomly divided into 6 groups:
1) Control group (Normal diet, n=8); Administered intragastrically with ultrapure water;
2) Model group (High fat diet, n=8); Administered intragastrically with ultrapure water;
3) Leonurine crystal form A in low dose group (High fat diet, n=8); Administered intragastrically at a dose of 4 mg/kg/day;
4) Leonurine crystal form A in middle dose group (High fat diet, n=8); Administered intragastrically at a dose of 8 mg/kg/day;
5) Leonurine crystal form A in high dose group (High fat diet, n=8); Administered intragastrically at a dose of 16 mg/kg/day;
6) Atorvastatin group (Positive control group, ApoE, High fat diet, n=8); Administered intragastrically at a dose of 2.5 mg/kg/day;

Rabbits were weighed before administered drugs every week, where the dosage of the drug for rabbits is calculate according to the weight; and housed in an air-conditioned room under (24±1° C. room temperature and 55±5% air humidity) and allowed enough food and water ad libitum. After 12 weeks of administration, the rabbits were fasted for 12 h, and blood (2 ml) was drawn from the marginal ear vein for hematology analysis. Hematology analysis: blood samples were let for standing for 2 h and centrifuged (3000 rpm, 10 min, 4° C.) to obtain serum. The serum samples were tested according to the protocols recommended by Nanjing Jiancheng Bioengineering Institute. The total cholesterol (TC), triacylglycerol (TG), low-density cholesterol (LDL-C) and how-density cholesterol (HDL-C) levels in the serum samples were assessed using automatic microplate reader and automatic biochemical analyzer. Statistical analysis: GraphPad Prism 5 software was used to analyze and draw figure. Results were expressed as the mean±standard (mean±SD), and statistical analysis was performed by one-way analysis of variance (ANOVA) or student's t test. A difference with $P<0.05$ was considered statistically significant. Statistical significance was set at *$P<0.05$, $P<0.01$, *$P<0.001$ versus the model group.

Figure 27:
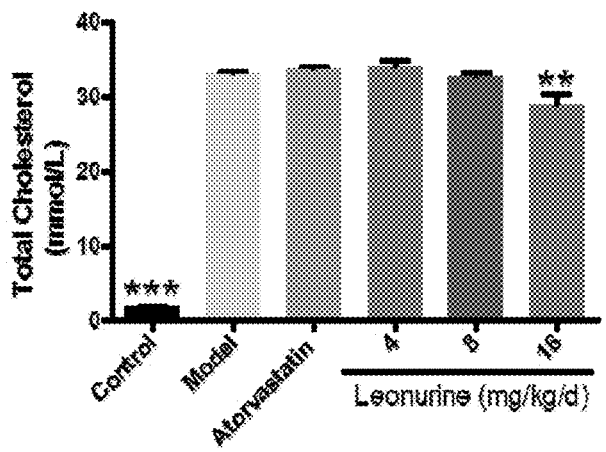
FIG. 27 shows that chronic continuous administration of leonurine crystal form A for 12 weeks could decrease the level of serum total cholesterol (TC) in the New Zealand white rabbit hyperlipidemia model. Total cholesterol (TC); Control; Model; Leonurine; , compared to the model group, P<0.01; *, compared to the model group, P<0.001.

The results showed that the total cholesterol in the serum of New Zealand white rabbit fed with high fat diet was higher than fed with normal diet. Leonurine crystal form A in high dose group reduced the total cholesterol in the serum compared with model group (vehicle group). However, the total cholesterol in the serum in atorvastatin group had no significant difference compared with model group. It indicated that the effects of leonurine crystal form A in high dose group to reduce total cholesterol were advanced than atorvastatin (FIG. 27).

Figure 28:
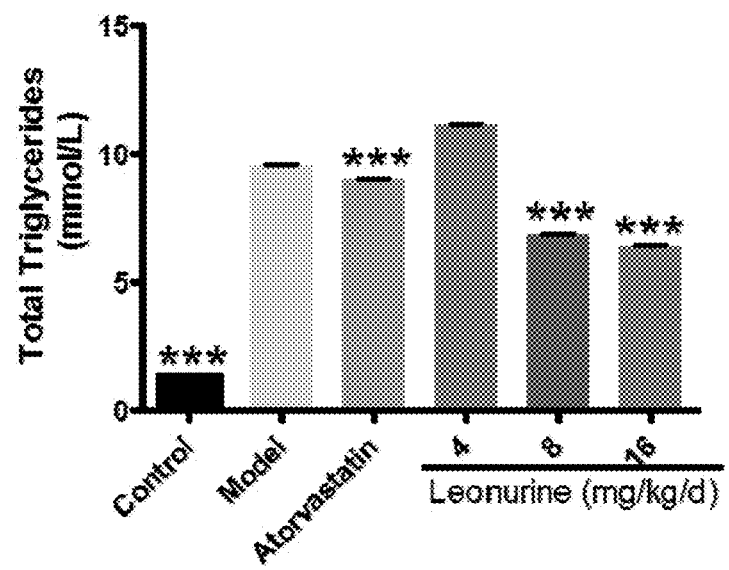
FIG. 28 shows that chronic continuous administration of leonurine crystal form A for 12 weeks could decrease the level of total triacylglycerol (TG) in the hyperlipidemia model of New Zealand white rabbit. Total triacylglycerol (TG); Control; Model; Leonurine; ***, compared to the model group, P<0.001.
Figure 29:
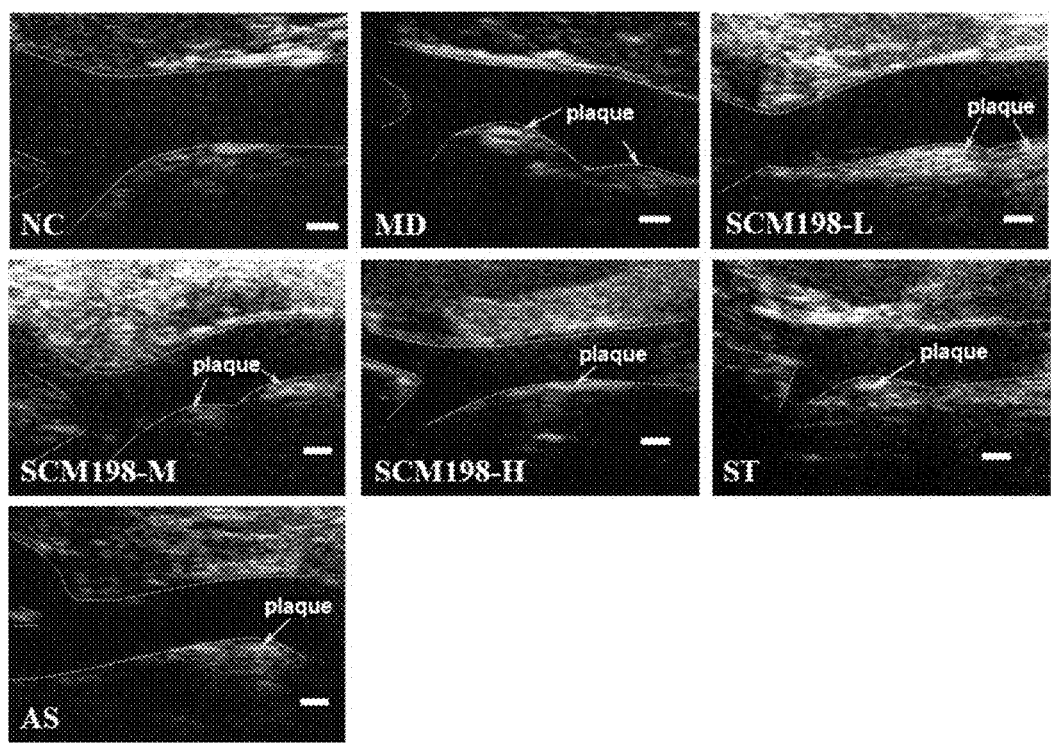
FIG. 29 is a Carotid atheromatous plaque micro-ultrasonographic which showed that atherosclerotic plaque formation at the bifurcation of the common carotid artery in each group was observed from the long axial section of the artery after 8 weeks of high-fat diet and administration, and the arrow points to the plaque in the thickening of the blood vessels. In the model group, the blood vessels were significantly thickened, and the plaque thickness of the drug group was significantly decreased and showed a dose-dependent effect.

The results showed that the triacylglycerol in the serum of New Zealand white rabbit fed with high fat diet was higher than fed with normal diet. Atorvastatin group and leonurine crystal form A in middle/high dose group both reduced the triacylglycerol in the serum compared with model group (vehicle group) (FIG. 28).

The results suggested that New Zealand white rabbits are highly susceptible to hyperlipidemia after giving a high-fat diet. However, chronic continuous administration of leonurine crystal form A could ameliorate the symptom of hyperlipidemia, including reduce total cholesterol and triacylglycerol in the serum, and better than the effect of Atorvastatin.

EXAMPLE 11

Experiment of Chronic Continuous Administration of Leonurine Crystal Form A Inhibited the Progression of Atherosclerotic Lesions in the Model of Hyperlipidemia Rabbits Forty-two male New Zealand rabbits weighed 2.0 to 2.5 kg were fed with normal diet to adapt to the housing environment for one week before experiment, and then the rabbits were fed with high fat diet (1% cholesterol; SF00-221 SpecialtyFeed Australia) for 8 weeks to establish the rabbit model of atherosclerosis. All the animals were randomly divided into 7 groups, and each group contains 6 rabbits: normal diet group (NC group), atherosclerosis model group (MD group), lipid lowering drug Atorvastatin positive control group (ST group, 2.5 mg/kg/day), anti-inflammatory drug aspirin positive group (ASP group, 25 mg/kg/day), leonurine crystal form A in low dose (SCM198-L group, 4 mg/kg/day), leonurine crystal form A in middle dose (SCM198-M group, 8 mg/kg/day) and leonurine crystal form A in high dose (SCM198-H group, 16 mg/kg/day). When the rabbits were started to give high fat diet, various drugs or vehicle (NC and MD groups) were simultaneously administered. The drug was administered once a day continuously for 8 weeks and weighed once a week to adjust the dose of drugs. Rabbits were caged in an air-conditioned room (24±1° C. room temperature and 55±5% air humidity) with 12 h light per day and had free access to water and were fed ad libitum. High-frequency ultrasound detection of carotid plaque: the high-frequency microscopy imaging system (Vevo770) was used to detect carotid atherosclerotic plaque at the end of the $8^{th}$ week of the experiment. The rabbits were anesthetized with 3% pentobarbital sodium in the dose of 30 mg/kg. Using the RMV707B probe (resolution 30 MHz) to observe the carotid bifurcation plaque and measure the blood flow velocity on the carotid artery long axis section by two-dimensional ultrasound. Then adjust direction of the probe so that the angle between the probe and the carotid artery is less than 60° to obtain the long-axis view. The intima-media thickness (IMT) is measured at the maximum end-diastolic plaque. The measurement to detected IMT is taking the vertical distance between the lumen-intimal echo to the medial-outer membrane echo, and detecting the atherosclerotic plaque on the right common carotid artery bifurcation proximal. The carotid ultrasound images and the maximum IMT at the plaque were analyzed, and the morphology of atherosclerotic plaques was evaluated. The data were analyzed by Vevo770 microscopy imaging system software. All measurements were repeated twice in the same area and averaged. The results showed that the mean IMT in MD group is higher than control group. Leonurine crystal form A significantly inhibited IMT growth induced by high fat and showed a dose-dependent effect. It indicates that leonurine crystal form A inhibited the formation of atherosclerotic plaques in a dose-dependent way.

EXAMPLE 12

According to a conventional method, the effective amount of leonurine crystal form A were added an appropriate amount of microcrystalline cellulose, starch or other excipients cosolvents were added as well to produce capsules, tablets, powders, granules, pills or other oral dosage forms.

The invention claimed is:

1. A crystalline form of leonurine hemisulfate wherein a powder X-ray diffraction pattern having characteristic peaks in degrees 2θ at 9.55°, 10.64°, 16.06°, 21.94°, 22.16°, 24.27°, 25.62° and 26.77°.

2. The crystalline form according to claim 1, wherein a powder X-ray diffraction pattern is shown in FIG. 15.

3. The crystalline form according to claim 1, wherein the crystalline form belongs to triclinic system, space group thereof is P-1, unit cell parameters thereof are a=7.857(5) Å, b=13.913(8) Å, c=17.314(10) Å, α=103.993(12)°, β=99.612(12)°, γ=100.482(15), and unit cell volume thereof is 1761.2(18) Å$^3$.

4. The crystalline form according to claim 1, wherein the crystalline form is obtained under a condition of, in the 25° C. suspension experiment, in a solvent of methanol, ethanol, isopropanol, acetone, acetonitrile, tetrahydrofuran, nitromethane, ethyl acetate, isopropyl acetate, isopentyl alcohol, methyl tert-butyl ether, toluene, methyl isobutyl ketone, n-hexane, n-heptane, ethyl ether, dichloromethane, trichloromethane, petroleum ether or water; or in the 50° C. suspension experiment, in a solvent if methanol, ethanol, acetone, methyl ethyl ketone, isopropyl acetate, methyl tert-butyl ether, toluene, n-hexane, n-heptane, ethyl ether, trichloromethane, petroleum ether or water; or in the 25° C. and 50° C. mixing solvent suspension and volatilization of some of solvents.

5. The crystalline form according to claim 1, wherein a powder X-ray powder diffraction pattern is shown in the following table,

| 2θ | Relative intensity (%) |
| --- | --- |
| 5.26 | 18.6 |
| 7.24 | 13.6 |
| 9.55 | 27.1 |
| 10.64 | 62.7 |
| 11.60 | 11.0 |
| 12.90 | 20.8 |
| 13.33 | 17.7 |
| 14.09 | 11.0 |
| 16.06 | 100.0 |
| 16.69 | 12.6 |
| 17.19 | 18.6 |
| 17.90 | 11.0 |
| 19.36 | 14.2 |
| 19.74 | 19.6 |
| 21.94 | 34.7 |
| 22.16 | 31.9 |
| 23.33 | 12.6 |
| 24.27 | 74.4 |

-continued

| 2θ | Relative intensity (%) |
|---|---|
| 25.62 | 86.4 |
| 26.46 | 10.7 |
| 26.77 | 30.6 |
| 29.68 | 10.4 |
| 31.28 | 8.8 |
| 35.45 | 9.8 |
| 36.95 | 9.1 |
| 38.02 | 8.2. |

* * * * *